(12) United States Patent
Bergman et al.

(10) Patent No.: US 7,467,631 B2
(45) Date of Patent: Dec. 23, 2008

(54) HAND HELD FLOSSING DEVICE

(76) Inventors: Mark Bergman, 13745 Seminole Dr., Chino, CA (US) 91710; David McCombs, 13745 Seminole Dr., Chino, CA (US) 91710

(*) Notice: Subject to any disclaimer, the term of this patent is extended or adjusted under 35 U.S.C. 154(b) by 252 days.

(21) Appl. No.: 10/805,766

(22) Filed: Mar. 22, 2004

(65) Prior Publication Data

US 2005/0000539 A1    Jan. 6, 2005

Related U.S. Application Data

(60) Provisional application No. 60/456,976, filed on Mar. 20, 2003.

(51) Int. Cl.
*A61C 15/00* (2006.01)

(52) U.S. Cl. .................................................. 132/325

(58) Field of Classification Search ......... 132/321–327; 264/445
See application file for complete search history.

(56) References Cited

U.S. PATENT DOCUMENTS

| | | | |
|---|---|---|---|
| 3,592,203 A | 7/1971 | Johnson | |
| 3,746,017 A | 7/1973 | Casselman | |
| 3,881,502 A | 5/1975 | Bennington | |
| 3,908,677 A | 9/1975 | Beach | |
| 3,927,687 A * | 12/1975 | Thierman | 132/325 |
| 4,005,721 A | 2/1977 | Yasumoto | |
| 4,008,728 A | 2/1977 | Sanchez | |
| 4,016,892 A | 4/1977 | Chodorow | |
| 4,151,851 A | 5/1979 | Bragg | |
| 4,178,947 A | 12/1979 | McCourry et al. | |
| 4,408,920 A | 10/1983 | Walther et al. | |
| 4,508,125 A | 4/1985 | Loubier | |
| 4,518,000 A | 5/1985 | Leverette | |
| 4,548,219 A | 10/1985 | Newman et al. | |
| 4,556,074 A | 12/1985 | Morin et al. | |
| 4,574,823 A | 3/1986 | Uriss | |
| 4,638,823 A | 1/1987 | Newman et al. | |
| 4,638,824 A | 1/1987 | De La Hoz | |
| 4,655,234 A | 4/1987 | Bowden | |
| 4,660,584 A | 4/1987 | Wofford | |
| 4,817,642 A | 4/1989 | Lipp | |
| 4,881,560 A | 11/1989 | Blank et al. | |
| 4,898,196 A | 2/1990 | Eason | |
| 4,920,993 A * | 5/1990 | Mackie | 132/324 |
| 4,995,361 A | 2/1991 | Lorenzana et al. | |

(Continued)

*Primary Examiner*—Robyn Doan
*Assistant Examiner*—Rachel A Running
(74) *Attorney, Agent, or Firm*—Knobbe, Martens, Olson & Bear

(57) ABSTRACT

An improved single-handed flossing device is provided which allows a user to use a high strength floss in order to obtain a relatively high floss tension between two tines of the device. The flossing device comprises a housing within which a floss supply, floss pathways, and a take-up mechanism are disposed. Actuation of the take up mechanism advances floss from the supply and through the pathways. The floss exits the housing and is exposed between a pair of housing tines. The exposed portion of floss is used by the user during flossing. A stop mechanism disposed between the supply floss and the take-up mechanism selectively restrains floss from being advanced. When the stop mechanism is engaged, actuation of the take-up mechanism applies tension to floss. The floss preferably has a relatively high strength, and the flossing device is configured in order to accommodate and capitalize on the characteristics of such high strength floss.

26 Claims, 18 Drawing Sheets

U.S. PATENT DOCUMENTS

| | | |
|---|---|---|
| 5,029,593 A | 7/1991 | Huttunen |
| 5,033,488 A | 7/1991 | Curtis et al. |
| 5,038,806 A | 8/1991 | Ewald |
| 5,040,554 A | 8/1991 | Rosenberger |
| 5,046,212 A | 9/1991 | O'Conke |
| 5,060,681 A | 10/1991 | Westbrook et al. |
| 5,063,948 A | 11/1991 | Lloyd |
| 5,085,236 A | 2/1992 | Odneal et al. |
| 5,105,840 A | 4/1992 | Giacopuzzi |
| 5,167,753 A | 12/1992 | McCullough et al. |
| 5,174,313 A | 12/1992 | Rosenberger |
| 5,209,251 A | 5/1993 | Curtis et al. |
| 5,220,932 A | 6/1993 | Blass |
| 5,226,435 A | 7/1993 | Suhonen et al. |
| 5,246,021 A | 9/1993 | Katz |
| 5,259,631 A | 11/1993 | Brands |
| 5,269,331 A | 12/1993 | Tanriverdi |
| 5,280,796 A | 1/1994 | Rosenberger |
| 5,280,797 A | 1/1994 | Fry |
| 5,284,169 A | 2/1994 | Gilligan et al. |
| 5,357,990 A | 10/1994 | Suhonen et al. |
| 5,375,614 A | 12/1994 | Navratil |
| 5,375,615 A | 12/1994 | Wahlstrom |
| 5,423,337 A | 6/1995 | Ahlert et al. |
| 5,495,863 A | 3/1996 | Bergman |
| 5,505,216 A | 4/1996 | Gilligan et al. |
| RE35,439 E | 2/1997 | Rosenberger |
| D380,869 S | 7/1997 | Bergman |
| 5,650,035 A | 7/1997 | McGaha et al. |
| 5,678,580 A | 10/1997 | Sherman |
| 5,680,876 A | 10/1997 | Hasham et al. |
| 5,682,911 A | 11/1997 | Harada |
| 5,722,439 A | 3/1998 | Endelson |
| 5,765,576 A | 6/1998 | Dolan et al. |
| 5,787,907 A | 8/1998 | Endelson |
| 5,819,768 A | 10/1998 | Bible et al. |
| 5,857,471 A | 1/1999 | Harada |
| 5,861,072 A * | 1/1999 | Medal ........................ 156/73.1 |
| 5,875,797 A | 3/1999 | Chiang et al. |
| 5,878,759 A | 3/1999 | Arias |
| 5,896,867 A | 4/1999 | McGaha et al. |
| 5,937,874 A | 8/1999 | Guay et al. |
| 5,967,153 A | 10/1999 | Mitha et al. |
| 6,039,054 A | 3/2000 | Park et al. |
| 6,065,479 A | 5/2000 | Chodorow |
| 6,080,481 A | 6/2000 | Ochs et al. |
| 6,155,274 A | 12/2000 | Stein |
| 6,220,256 B1 | 4/2001 | Dolan et al. |
| 6,227,210 B1 | 5/2001 | Wyss |
| 6,253,774 B1 | 7/2001 | Mason |
| 6,289,904 B1 * | 9/2001 | Suhonen et al. ............. 132/321 |
| 6,497,237 B1 * | 12/2002 | Ali .............................. 132/324 |
| 6,874,509 B2 | 4/2005 | Bergman |
| 7,011,099 B2 * | 3/2006 | Bergman ..................... 132/325 |
| 2002/0145066 A1 | 10/2002 | Schweigert |
| 2002/0170570 A1 * | 11/2002 | Bergman ..................... 132/322 |

* cited by examiner

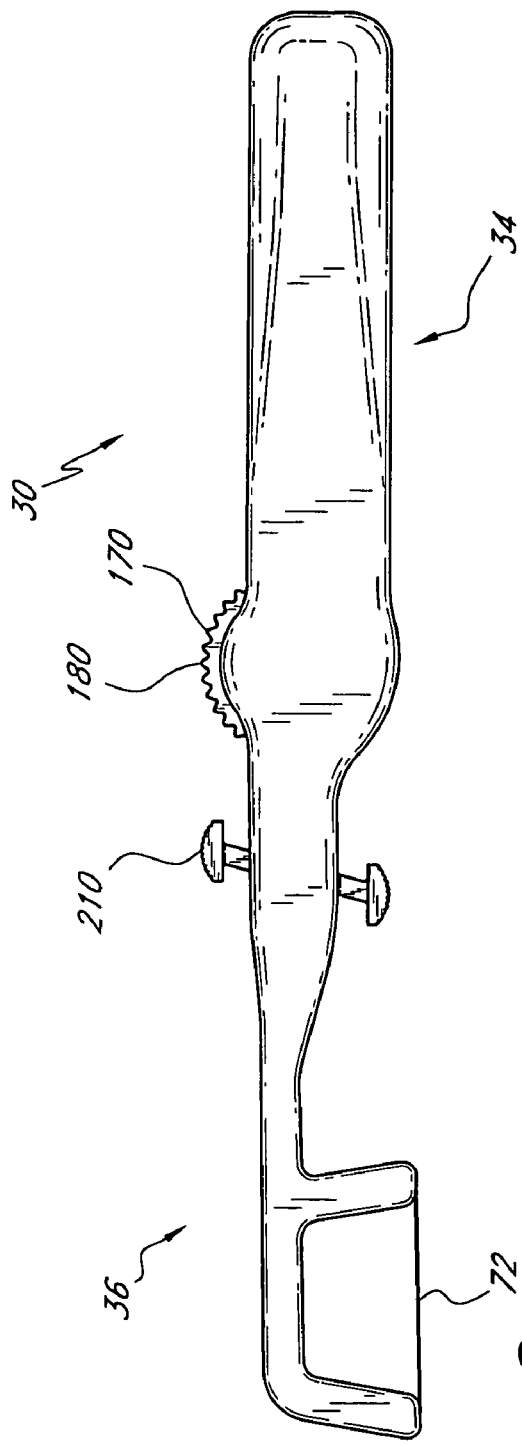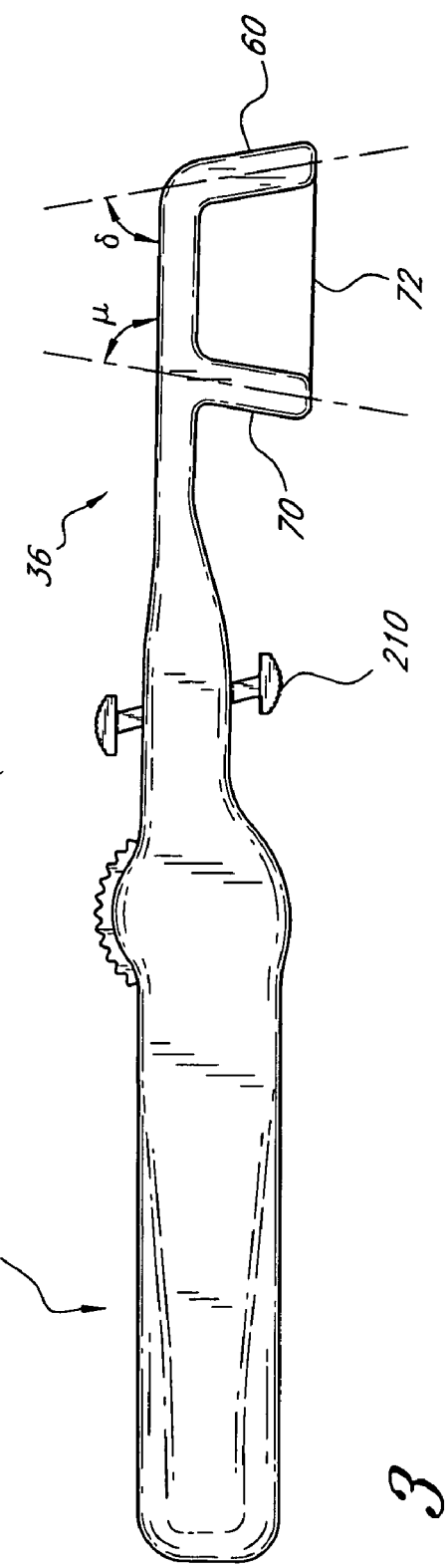
FIG. 2
FIG. 3

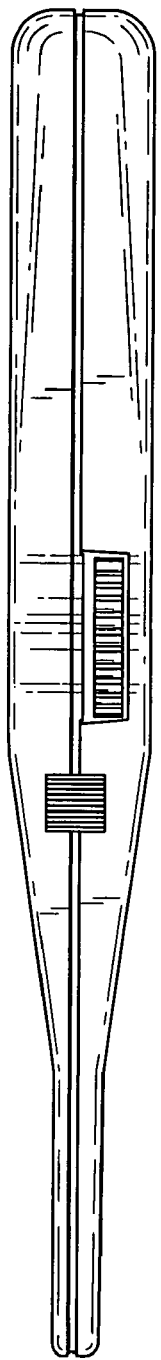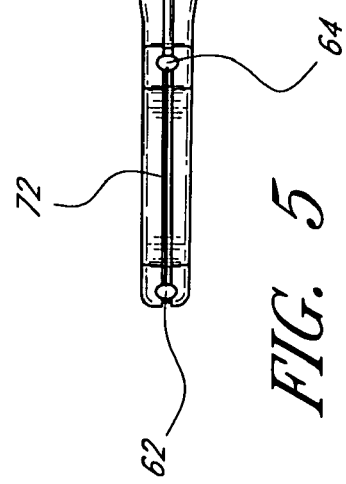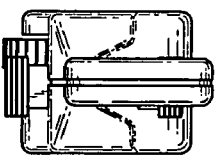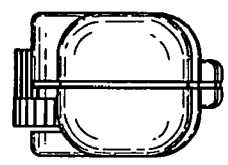
FIG. 4
FIG. 5
FIG. 6
FIG. 7

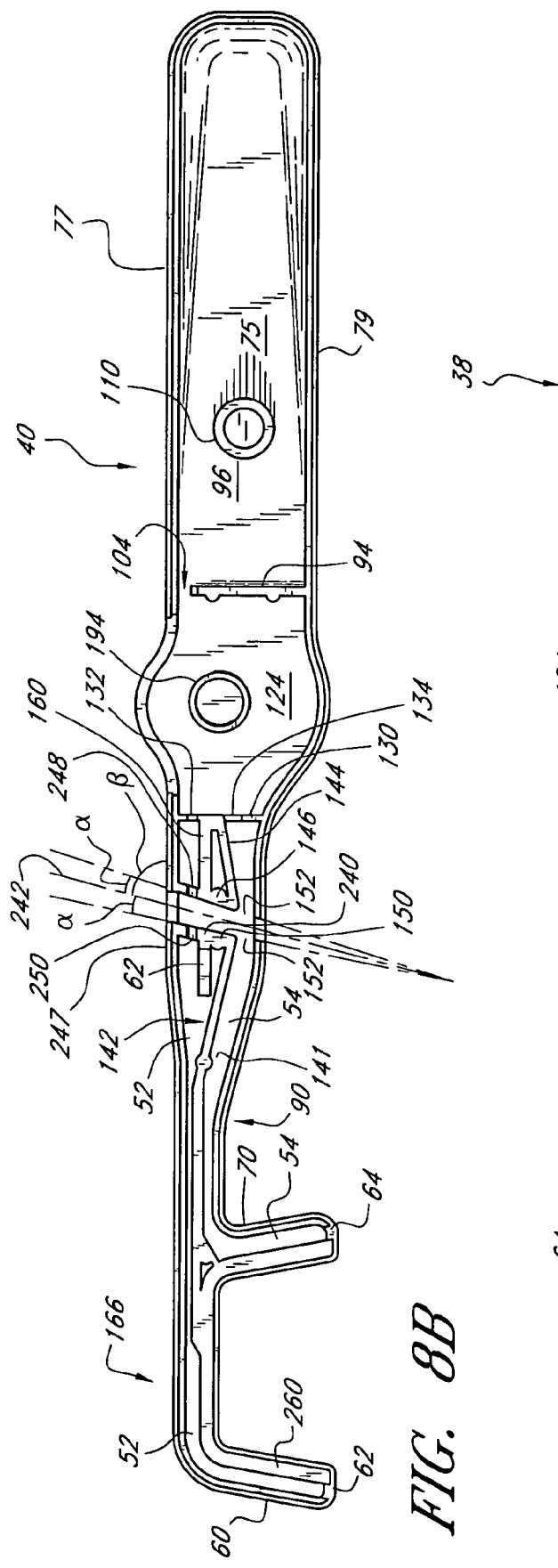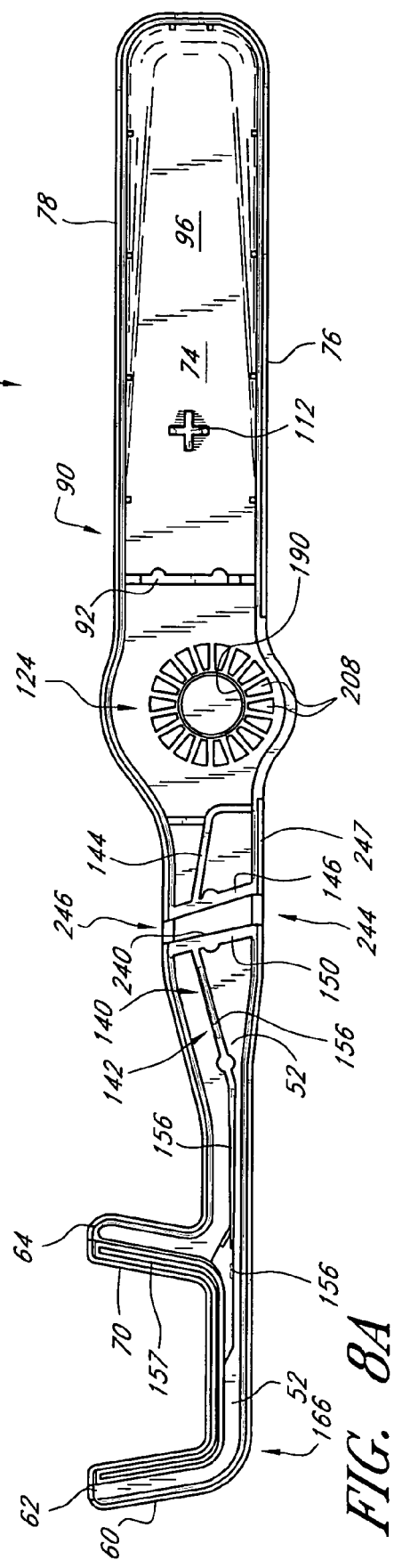
FIG. 8B
FIG. 8A

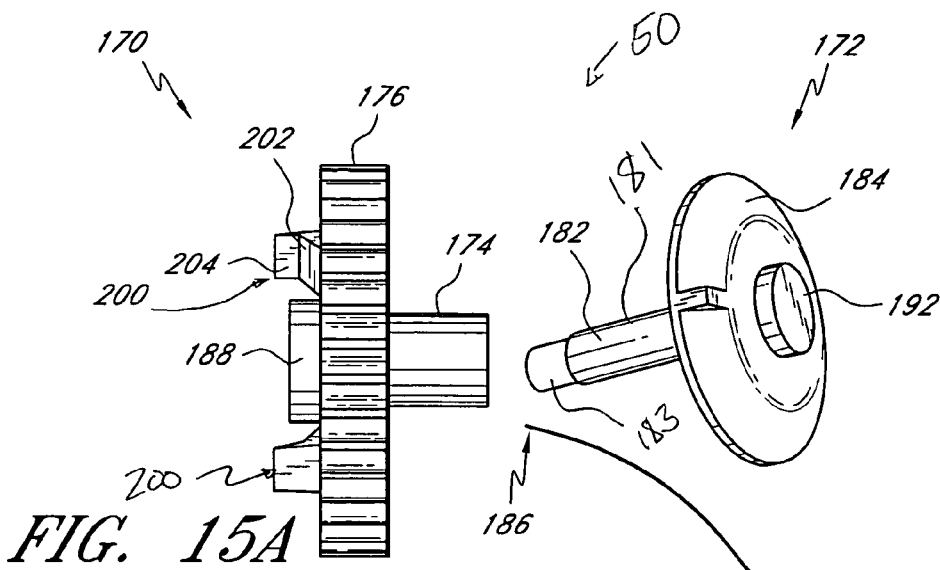
*FIG. 15A*
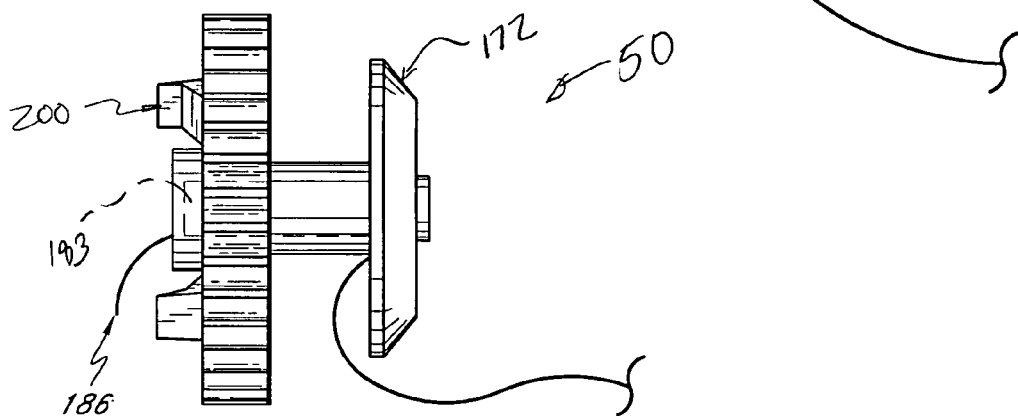
*FIG. 15B*
*FIG. 15C*
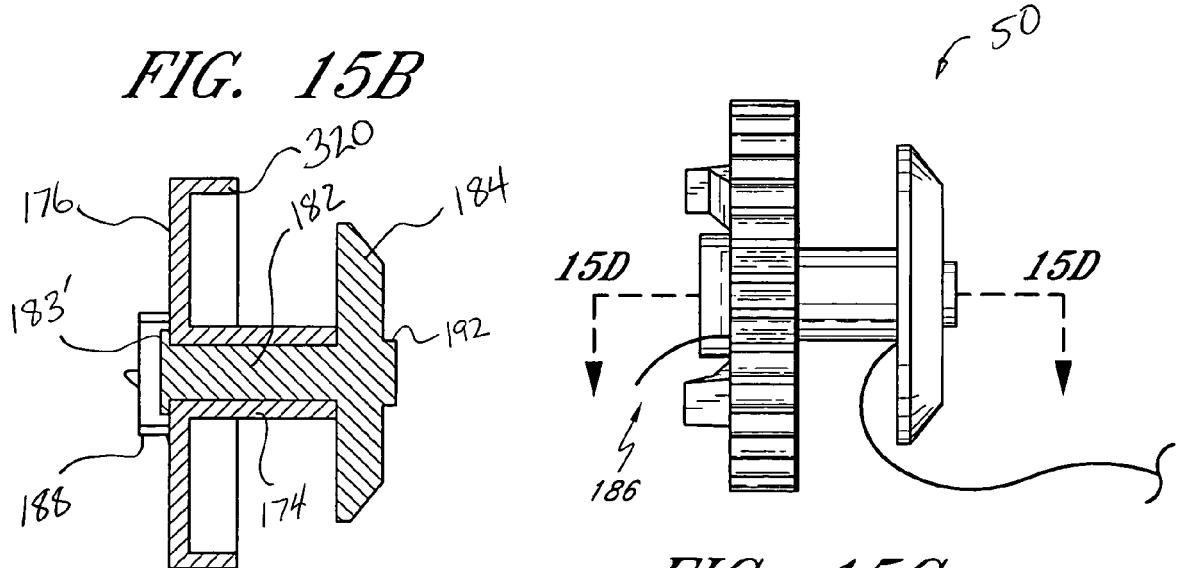
*FIG. 15D*

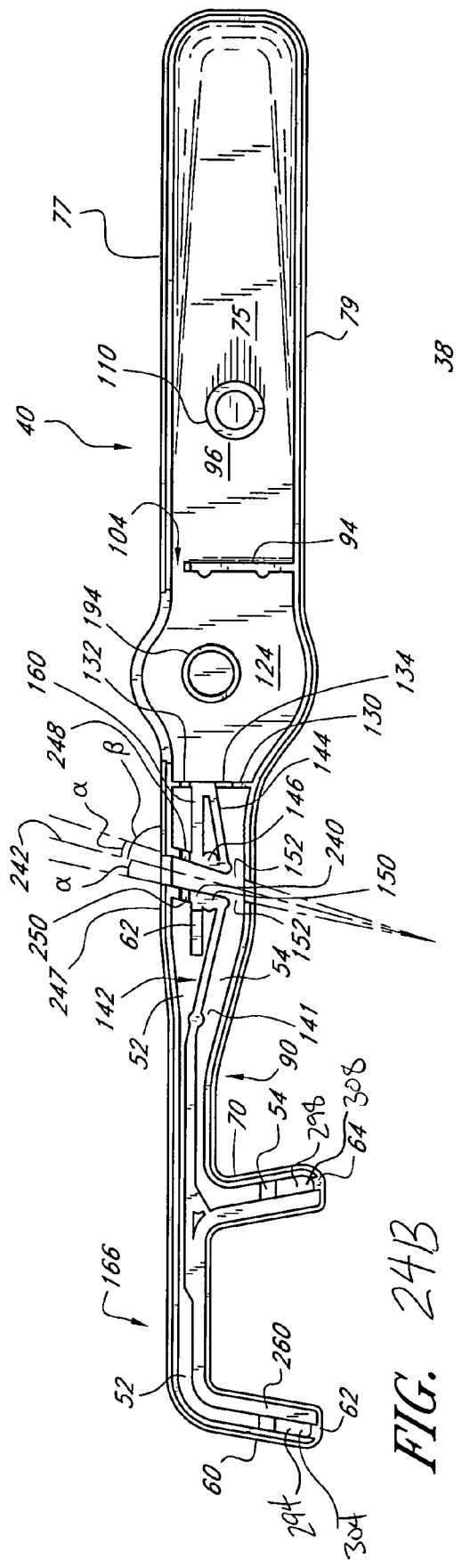
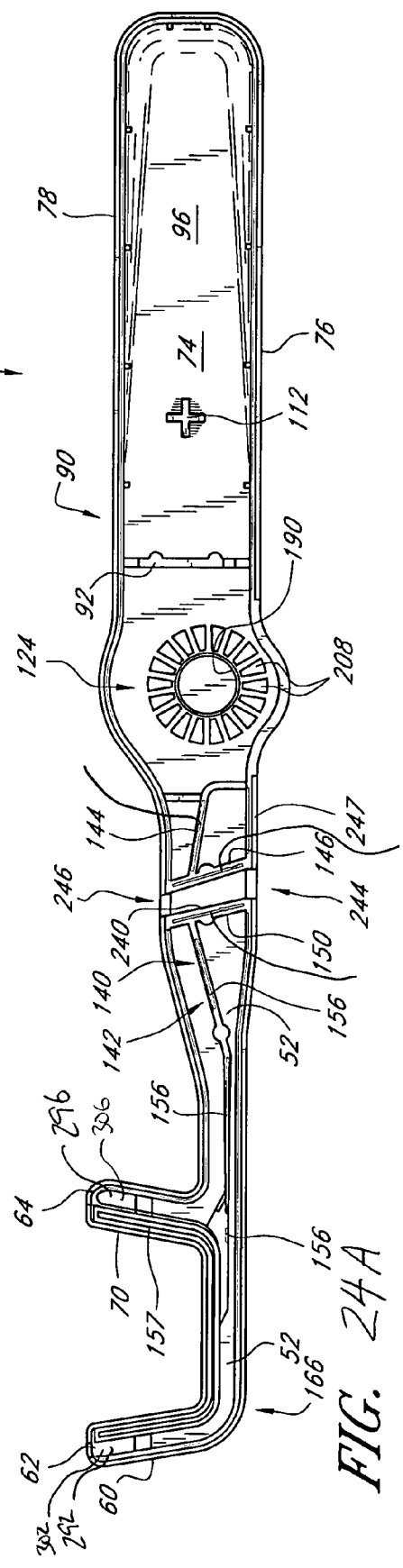

HAND HELD FLOSSING DEVICE

RELATED APPLICATION

This application is based on and claims priority to U.S. Provisional Application Ser. No. 60/456,976, which was filed on Mar. 20, 2003. The entirety of this priority application is hereby incorporated by reference.

BACKGROUND OF THE INVENTION

1. Field of the Invention

The present invention relates to a hand-held flossing device. More particularly, the invention relates to a hand-held flossing device with a tensioning mechanism.

2. Description of the Related Art

Flossing regularly is important to dental health. Traditionally, flossing has been accomplished by holding the floss tightly between the user's hands, wrapping the floss about the user's fingers, and winding the floss through the user's teeth. This method of flossing is cumbersome in several ways. For example, it is difficult to reach back teeth, it is also difficult to achieve a sufficient floss tension without hurting one's hands. Additionally, the user's hands touch the floss and enter the math, thus germs and other matter that may be on the user's hands can be transferred to the user's mouth. Similarly, the floss tends to communicate saliva and flossing products, such as dislodged plaque and dental caries, from the user's mouth to the hands.

To simplify flossing and avoid some of these problems, flossing aids have been developed. These aids employ different approaches to holding floss. Such flossing aids have been largely unsuccessful due to many factors such as difficulty of use, tendency to break, expense, inability to maintain appropriate tension, and the like. As such, there is a need in the art for a hand-held flossing device that is sturdy, inexpensive, easy to operate, and which delivers consistent and controllable performance during flossing.

SUMMARY OF THE INVENTION

In accordance with one embodiment, the present invention provides a hand-held flossing device comprising a housing having a handle portion and a head portion. The housing supporting a floss supply comprising a floss, a floss path, a floss advancement mechanism configured to selectively advance floss from the floss supply and through the path, and a stop mechanism. The stop mechanism is configured to selectively engage at least a portion of the floss to resist advancement of the floss upon actuation of the advancement mechanism so that a tension is imparted to the floss between the stop mechanism and the advancement mechanism. The floss comprises a first surface coating comprising a water soluble material and a second surface coating comprising a generally non-water soluble material. The second coating substantially encapsulates the first coating.

In accordance with another embodiment, a hand-held flossing device is provided comprising a housing having a handle portion and a head portion. A series of ratchet receiver members are integrally formed with the housing. A floss supply is provided and comprises a floss. A floss supply path is defined within the housing between the floss supply and a floss exit formed in the head portion. A floss return path is defined within the housing between a floss entrance and an advancement mechanism. Floss is directed through the floss supply and return paths, the floss exiting through the exit and reentering through the entrance. An exposed floss portion extends between the exit and entrance. The advancement mechanism is configured to selectively advance floss from the supply and through the supply and return paths. The advancement mechanism comprises a ratcheting member adapted to engage the series of ratcheting receiver members of the housing.

In accordance with yet another embodiment, the present invention provides a hand-held flossing device comprising a housing having a handle portion and a head portion. The housing defines a floss path therein. A floss supply comprises floss wound about itself. An advancement mechanism is configured to selectively pull floss through the floss path and draw floss from the supply. The device is configured so that floss unwinds from the floss supply when the advancement mechanism draws the floss from the supply, and the floss on the supply otherwise is not under tension. The floss comprises a surface coating configured to mildly bond adjacent windings of the floss such that the windings on the floss supply will not spontaneously unwind substantially when the supply is not under tension.

In accordance with still another embodiment, a hand-held flossing device comprises a housing comprising a handle portion and a head portion. The head portion has an elongate back, a distal tine extending downwardly and distally at an angle of about 78-81° relative to the back, and a proximal tine extending downwardly and proximally at an angle of about 78-81° relative to the back. A floss is disposed in the housing and is movable therethrough along a path. A portion of the floss exits the housing through one of the distal and proximal tines and reenters the housing through the other of the distal and proximal tines. A tensioning member is configured to selectively impart a tension on the floss.

In accordance with still another embodiment of the present invention, a hand-held flossing device comprises a housing having a handle portion and a head portion. The housing supports a floss supply, a floss path, a floss take-up mechanism configured to selectively advance floss from the floss supply and through the path, and a stop mechanism. The stop mechanism is configured to selectively grip at least a portion of the floss to resist advancement of the floss upon actuation of the take-up mechanism so that a tension is imparted to the floss between the stop mechanism and the take-up mechanism. The head comprises a floss exit and a floss entrance. The exit and entrance are configured so that floss disposed along the floss path exits the housing at the floss exit and reenters the housing at the floss entrance so that an exposed portion of the floss is outside of the housing between the exit and entrance. The head has an inner wall portion and an outer wall portion, the inner wall portion having a thickness greater than the outer wall portion. The take-up mechanism and stop mechanism are configured to impart at least 4 pounds of tension to the floss.

In accordance with still a further embodiment, a hand-held flossing device comprising a housing having a handle portion and a head portion is provided. A floss supply comprising a floss is also provided. A floss supply path is defined within the housing between the floss supply and a floss exit formed in the head portion. A floss return path is defined within the housing between a floss entrance and an advancement mechanism. The advancement mechanism is configured to selectively advance floss from the floss supply and through the supply and return paths. The housing is arranged and configured to include an enclosed truss structure.

All of these aspects and advantages are intended to be within the scope of the invention disclosed herein. These and other aspects of the present invention will become readily apparent to those skilled in the art in the following detailed description of preferred embodiments having reference to the attached figures. The invention is not limited to any particular preferred embodiment(s) disclosed.

BRIEF DESCRIPTION OF THE DRAWINGS

FIG. 2 is a left side view of the flossing device of FIG. 1.
FIG. 3 is a right side view of the flossing device of FIG. 1.
FIG. 4 is a top view of the flossing device of FIG. 1.
FIG. 5 is a bottom view of the flossing device of FIG. 1.
FIG. 6 is a front view of the flossing device of FIG. 1.
FIG. 7 is a rear view of the flossing device of FIG. 1.
FIG. 8A shows the inside of a first segment of the flossing device of FIG. 1.
FIG. 8B shows the inside of a second segment of the flossing device of FIG. 1.
FIG. 15A shows the take up wheel and cap during assembly.
FIG. 15B shows the take up wheel and cap midway through assembly.
FIG. 15C shows the take up wheel and cap assembled.
FIG. 15D is a cross sectional view taken along line 15D-15D of FIG. 15C.
FIG. 24A shows the inside of a first segment of the another embodiment of a flossing device.
FIG. 24B shows the inside of a second segment of the flossing device of FIG. 24A.

DETAILED DESCRIPTION OF PREFERRED EMBODIMENTS

Figure 1:
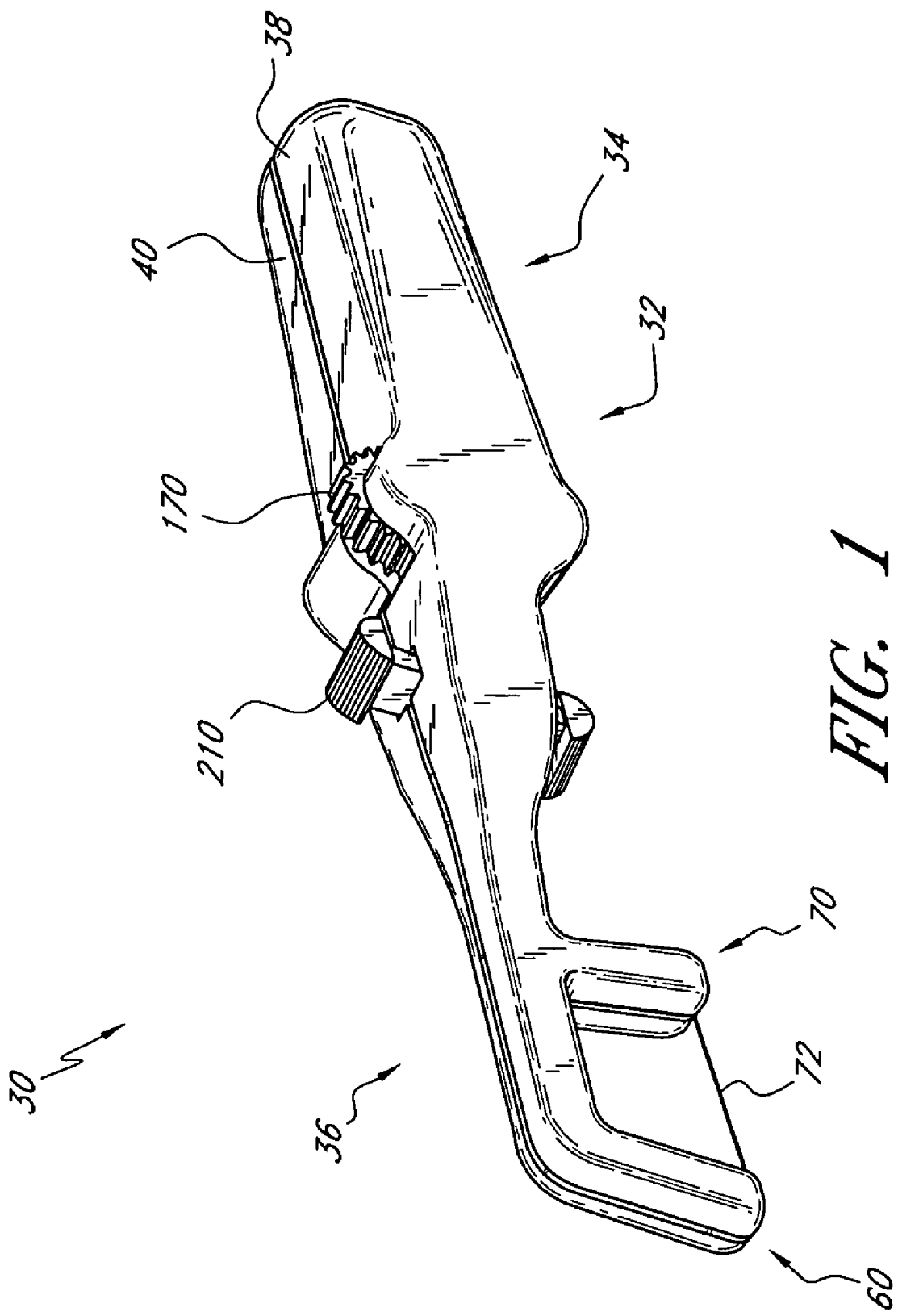
FIG. 1 is a perspective view of the flossing device having aspects of the present invention.

With reference first to FIGS. 1-10, an embodiment of a flossing device 30 employing aspects of the present invention will be discussed in summary prior to describing portions and aspects of the device in greater detail. The illustrated flossing device 30 shares certain aspects with applicant's co-pending U.S. application Ser. No. 09/861,254, filed May 18, 2001, entitled Flossing Device with Advancing and Tensioning Mechanism, and applicant's U.S. Pat. No. 5,495,863, also entitled Flossing Device with Advancing and Tensioning Mechanism. The patent and co-pending application are hereby incorporated by reference in their entirety.

The illustrated flossing device 30 comprises an elongated housing 32 having a handle portion 34 and a head portion 36. The housing 32 comprises first and second separately-formed segments 38, 40. Preferably the segments 38, 40 are formed by injection molding, although other manufacturing processes can be used. The segments are configured to matingly cooperate with one another to form the housing 32. The housing 32 encloses a floss supply 42, stop mechanism 44 and take-up mechanism 50, as well as a floss supply path 52 and a floss return path 54. The floss supply 42 is disposed within the handle portion 34 of the housing 32, and floss 56 from the supply 42 extends along the supply path 52 to a distal tine 60 in the head 36 of the flosser 30. The supply floss 56 exits the distal tine 60 at a path exit 62 and re-enters the housing 30 at a return path entrance 64 disposed in a proximal tine 70. From the return path entrance 64 the floss, now termed return floss 58, follows the return path 54 to the take-up mechanism 50. The floss 56, 58 is maintained within the housing 30 when following the supply and return paths 52, 54, but is exposed between the supply path exit 62 and return path entrance 64. This exposed floss 72 is available to be used for flossing by the user.

The take-up mechanism 50 and stop mechanism 44 cooperate to apply a tension to the floss 56 so that the exposed floss 72 is tensioned as desired by the user. When the floss is locked in place by the stop mechanism 44, winding of the take-up mechanism 50 selectively applies a variable tension to the floss.

Figure 9:
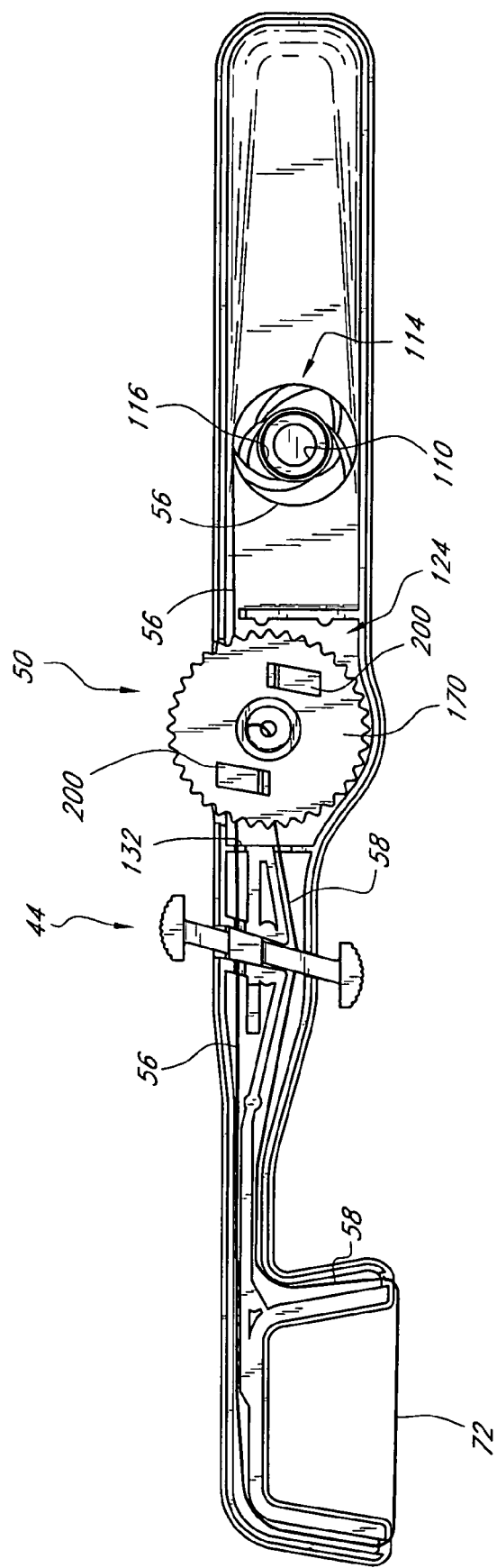
FIG. 9 shows the second segment of FIG. 8B partially assembled.
Figure 10:
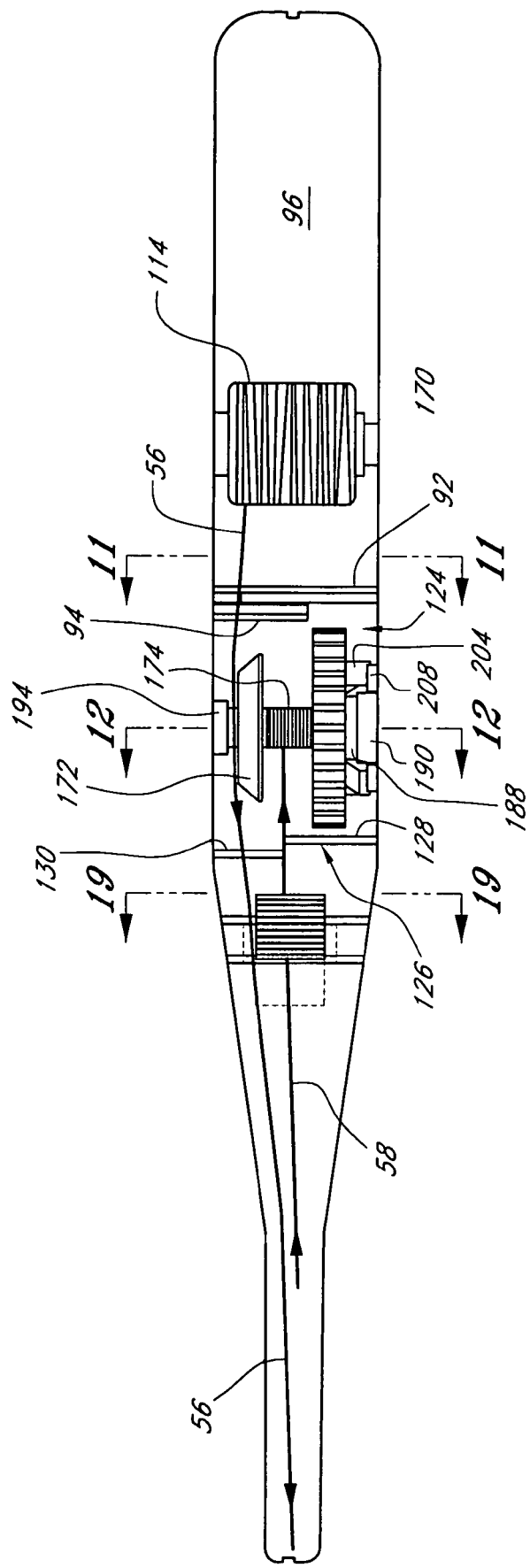
FIG. 10 is a top view of the flossing device of FIG. 1 showing various internal components and the path of floss.

With more specific reference to FIGS. 8-10, each of the first and second segments 38, 40 has a side wall 74, 75, top wall 76, 77, and bottom wall 78, 79, each having inner and outer surfaces 80, 82. Additionally, each segment 38, 40 has a peripheral edge 40 along which the segments 38, 40 mate when assembled together to form the housing 30.

Figure 11:
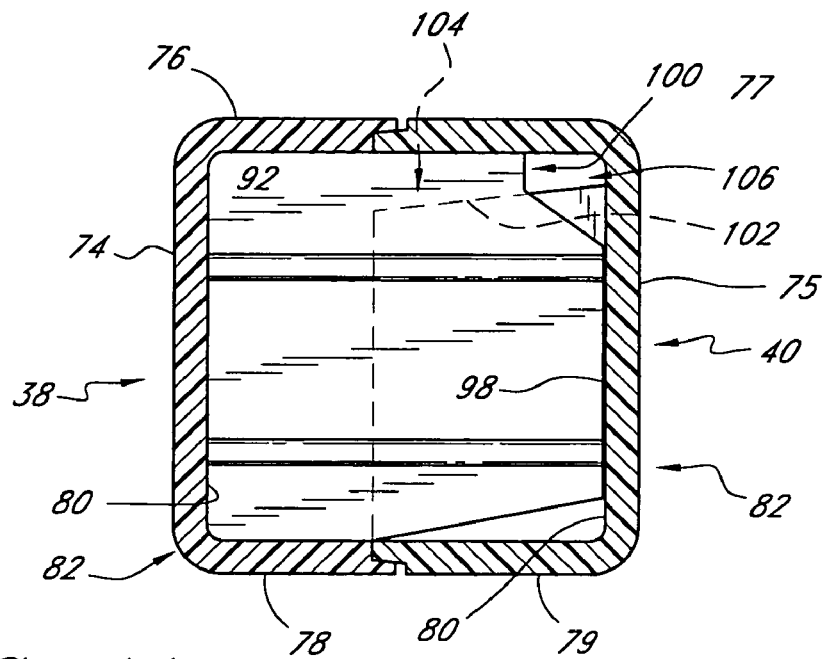
FIG. 11 is a cross-section of the flossing device of FIG. 10 taken along line 11-11.

With continued reference to FIGS. 8-10, the first segment 38 has a back wall portion 92 and the second segment 40 also has back wall portion 94. The portions 92, 94 cooperate with one another to define a first compartment 96 within the housing handle 34. With reference also to FIG. 11, the first segment back wall 92 extends from the side wall 74 and terminates at a free edge 98 that extends beyond the peripheral edge 90 of the segment 38. In this manner, when the segments are assembled, the free edge 98 is disposed immediately adjacent the second segment 40 side wall 75. A notch 100 is formed in the top portion of the free edge 98.

The second segment back wall 94 also extends from the side wall 75 of the second segment 40, but terminates at about the peripheral edge 90 of the segment 40. A top edge 102 of the back wall 94 is spaced from the top wall 77 of the segment 40. Preferably, the top edge 102 of the back wall 94 is configured so that the space 104 is generally "V" shaped.

In the illustrated embodiment, the back wall 94 in the second segment 40 is disposed forwardly relative to the position of the back wall 92 in the first segment 38. As such, and as shown in FIG. 11, the walls overlap each other when the segments are assembled. Further, the second segment back wall notch 100 cooperates with the first segment back wall, space 104 to define an opening 106 through the back wall. This opening 106 is directed adjacent the second segment side wall 75.

A transverse post 110 extends from the second segment side wall 75 and is configured to engage a seat 112 that extends from the first segment side wall 74. A floss supply spool 114 is disposed on the post 110. The spool 114 comprises a hollow axle 116 upon which floss 56 is wound. The axle 116 is rotatable about the post 110 so that the supply floss 56 can be dispensed from the spool 114. As best shown in FIGS. 9-11, the floss 56 extends from the supply spool 114 and through the opening 106. Since the opening 106 is disposed adjacent the second segment side wall 75, the supply floss 56 exiting the first compartment 96 through the opening 106 is directed immediately adjacent the side wall 75.

A second compartment 124 is defined between the back wall and an intermediate wall 126. The return floss take-up mechanism 50 is disposed generally within the second compartment 124. The take-up mechanism 50 will be discussed in further detail below.

With specific reference next to FIGS. 8-10 and 12, the first and second segments 38, 40 each have intermediate wall portions 128, 130 which cooperate to define the intermediate wall 126. In the illustrated embodiment, the first segment intermediate wall portion 126 is generally solid, without apertures formed therethrough. In contrast, the second segment intermediate wall portion 128 has a generally "V" shaped slot 132 adjacent the top of the wall portion 128. The "V" shaped slot 132 extends to immediately adjacent the second segment side wall 75. Supply floss 56 from the first compartment 96, which enters the second compartment 124 adjacent the second segment side wall 75, crosses through the second compartment 124 and exits the second compartment through the "V" shaped slot 132 in the intermediate wall 126. While extending through the second compartment 124, the supply floss remains generally adjacent the second segment side wall 75. It is to be understood that the "V" shaped slot discussed above, and other "V" shaped members discussed herein, can have other, similar shapes, such as a "U" shape.

A floss return slot 134 is also formed through the second segment intermediate wall portion 128. The floss return slot 134 cooperates with the first segment intermediate wall portion 126 to define a return floss opening 136. As shown in the drawings, the return floss 58 passes from the return path 54 through the return floss opening 136 and into the second compartment 124, where it is wound upon the take-up mechanism 50. In the illustrated embodiment, the "V" slot 132 and return floss slot 134 are positioned relative to one another so that the supply floss 56 and return floss 58 pass through the intermediate wall 126 at locations that are vertically and transversely spaced from one another.

With continued specific reference to FIGS. 8-10, each segment 38, 40 comprises an elongate rib portion 140, 141. The rib portions of the opposing segments cooperate with one another when assembled to form an elongate rib 142. A first portion 144 of the elongate rib extends from the intermediate wall 126 to a stop mechanism back wall 146; a second portion 148 of the elongate rib extends from a stop mechanism front wall 150 to the head portion 36 of the device. The elongate rib 142 separates the supply path 52 from the return path 54. As such, supply and return floss 56, 58 are completely separated from one another within the housing 32 along the length of the elongate rib 142. With specific reference to FIGS. 8B and 9, the stop mechanism front and back walls 150, 146 do not extend below the rib 142. As such, spaces 152 are defined through which the return floss path 54 extends.

With specific reference to FIG. 8A, the first segment elongate rib portion 140 comprises energy directors 156 in the form of relatively thin portions of material extending along a mating edge of the rib portion 140. More specifically, the energy directors 156 are configured to melt more readily than the adjacent rib portions 140, 141, and thus help to weld the rib portions thoroughly together without comprimising structural integrity of the rib. In one embodiment, the first and second segments 38, 40 are assembled and then sonic welded in order to bond them together. The energy directors 156 more thoroughly establish the bond between the opposing rib portions 140, 141 during sonic welding in order to form the elongate rib 142. As such, the elongate rib is quite strong, and there is little or no likelihood of gaps between the rib portions 140, 141 which would result in failed separation of the return and supply floss paths 52, 54 and which would weaken the device. The elongate rib provides strength and rigidity to the flossing device. Such strengthening of the flossing device assists in consistent operation of the stop mechanism, as will be discussed in more detail below.

With continued reference to FIG. 8B, a second rib portion 60 extends between the intermediate wall portion 126 and the stop mechanism back wall 146 in the second segment 40. As such, a truss structure is formed in the second segment 40 by the second rib portion 160, first rib portion 144, intermediate wall portion 126, and stop mechanism back wall 146. A third rib portion 162 extends from the stop mechanism front wall 150 in the second segment 40.

As discussed above, the elongate rib 142 extends to the head portion 36 of the device. The head portion 36 comprises a back portion 166 and distal and proximal tines 60, 70. The supply path 52 is defined within the housing 32 through the back portion 166 and distal tine 60. Supply floss 56 exits the distal tine 60 at the supply path exit 62 and enters the proximal tine 70, as used floss 58, at the return path entrance 64. The return floss path 54 communicates used floss 58 to the handle 34 of the device.

Figure 13A:
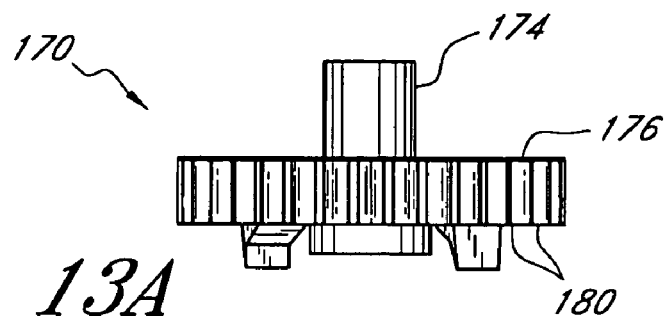
FIG. 13A is a side view of a take-up wheel.
Figure 13B:
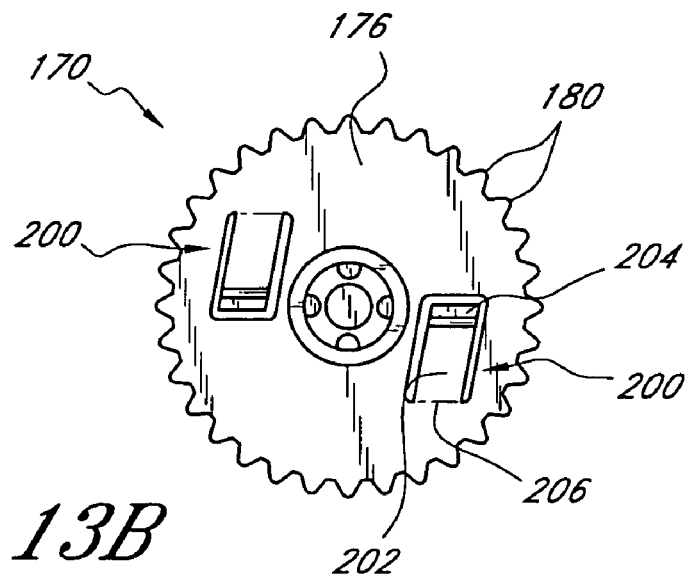
FIG. 13B is an end view of the take up wheel of FIG. 13A.

As discussed above, and with reference next to FIGS. 9, 10 and 13-15, return floss 58 that enters the second compartment 124 is wound upon the take-up mechanism 50. In the illustrated embodiment, the take-up mechanism comprises a take-up wheel 170 and a cap 172. With specific reference to FIGS. 13A and B, the take-up wheel 170 comprises a hollow axle portion 174 and a wheel portion 176. Serrations 180 are provided about a peripheral circumference of wheel portion 174.

Figure 14:
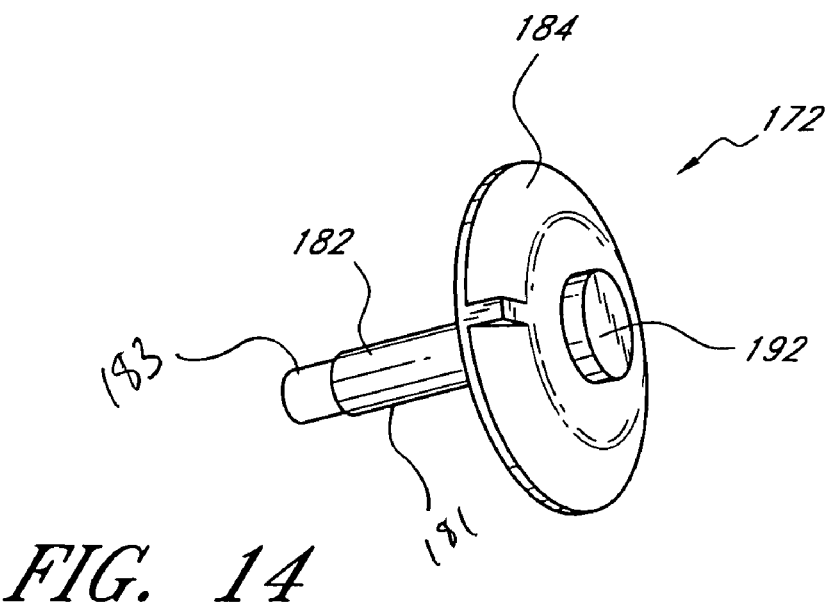
FIG. 14 is a perspective view of a take up wheel cap.

With specific reference next to FIG. 14, the cap portion 172 comprises a transverse axle portion 182 and a disk 184. The cap axle 182 comprises a textured portion 181 and a tip portion 183. Preferably, the textured portion 181 comprises a non-smooth surface. The cap axle 182 is configured to fit within the hollow take-up wheel axle 174 as shown in FIGS. 15A-D.

As shown particularly in FIGS. 15A-D, the take-up mechanism 50 is assembled by advancing a free end 186 of the return floss 58 and the cap axle 182 into the hollow take-up wheel axle 174 until fully inserted therein as shown in FIG. 15B. Once the take-up wheel 170 and cap 172 are assembled, the respective axles preferably are bonded together. In one embodiment, the axles are bonded by applying heat to melt the materials together. For example, FIG. 15B shows the tip 183 extending partially from the hollow take-up wheel axle 174. Preferably, a heating element is applied to the tip 183 so as to melt the tip to the melted arrangement 183' shown in FIGS. 15C and D. Preferably, the heat also at least partially melts the textured surface of the textured portion 181 to help melt-bond the cap axle 182 to the inner wall of the take-up wheel axle 174, and to help bond the floss to the take-up wheel/cap assembly.

Since the components of the take-up assembly 50 are generally well bonded to one another, the take-up mechanism 50 can exert relatively high tension on floss 58 during winding without the floss becoming detached from the wheel 170. It is to be understood that other methods and apparatus such as, for example, adhesives and welding, can be used for bonding the take-up wheel and cap.

Figure 12:
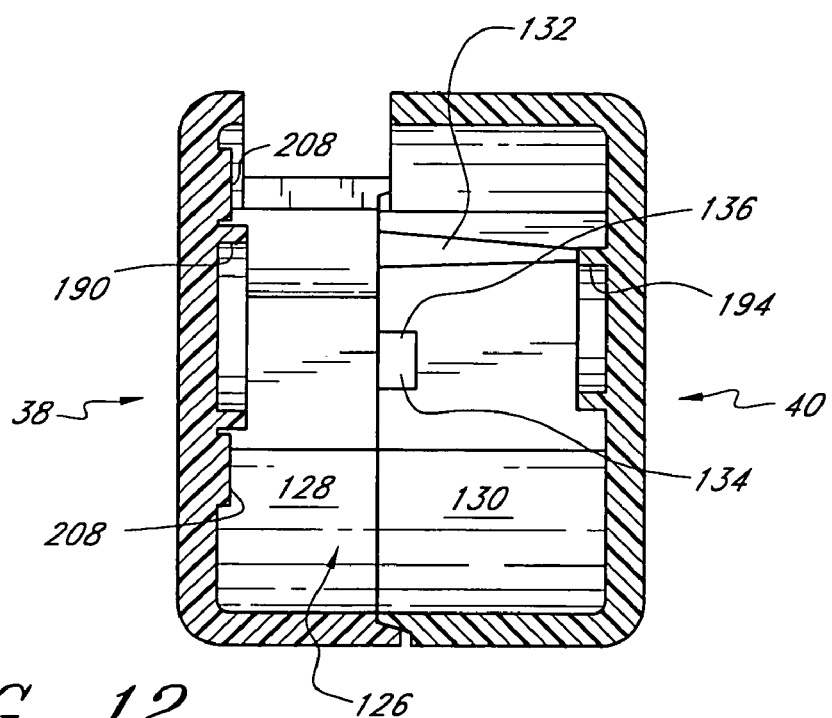
FIG. 12 is a cross-section of the flossing device of FIG. 10 taken along line 12-12.

With reference again to FIGS. 13A and B, the take-up wheel 170 has a mounting portion 188 extending therefrom on a side of the wheel 170 opposite the axle 174. As shown in FIGS. 8A, 10, and 12 the first housing side wall 74 includes an axle mount 190 that is configured to be complementary to the mounting portion 188 of the wheel 170 so as to rotatably support the wheel 170. Similarly and as shown in FIG. 14, a mounting portion 192 extends from the cap disk on the side of the disk 184 opposite the cap axle 182. As shown in FIGS. 8B, 10, and 12, the second housing side wall 75 includes a mount 194 that is complementary to the disk mounting portion 192 and rotatably supports the mounting portion 192 therewithin. As such, the assembled take-up mechanism 50 is rotatably supported by the housing 32.

As shown in FIGS. 1-7 and 10, a portion of the take-up wheel 170 extends out of the housing 32 when installed. The take-up wheel 170 is thus accessible and actuable by a user's thumb holding onto the handle portion 34 of the housing 32.

With reference again to FIGS. 8A, 12 and 13A and B, the take-up wheel 170 has a pair of pawls 200. The pawls 200 each include an elongate arm 202 and a latch portion 204 extending outwardly from the arm 202. The arms 202 connect to the wheel 170 at a hinge portion 206, and are biased outwardly from the wheel 170.

A series of ratchet receivers comprise protuberances 208 that extend from the first segment side wall 74 and are arranged circumferentially around the mount 190. When the take-up wheel 170 is installed, the pawls 200 interact with the protuberances 208 in order to create a one-way ratcheting mechanism. More specifically, the pawl latches 204 and the protuberances 208 are configured so that as the take-up wheel 170 is rotated in a tightening rotational direction, the pawls 200 are moveable over the protuberances 208, but when the wheel is urged in the opposite rotational direction, the latches 204 engage the protuberances 208 and prevent rotation. As such, the take-up mechanism is ratcheted.

In the illustrated embodiment, the pawls 200 are integrally formed with the take-up wheel 170, and the protuberances 208 are integrally formed with the first housing 38. It is to be understood that, in another embodiment, the ratcheting mechanism can have a different structure.

With reference next to FIGS. 9 and 10, floss 58 from the return path 54 winds upon the take-up wheel axle 174 between the wheel portion 176 and the cap 172. Supply floss 56 that travels from the first compartment 96 through the second compartment 124 and into the supply path 52 is directed along the side wall 75 of the housing 32 on an opposite side of the disk 184 from the used floss 58 which is wound about the axle 75. As such, the used return floss 58 and unused supply floss 56 are kept separate from one another. In operation, rotation of the take-up wheel 170 winds return floss 58 around the axle 174 and draws supply floss 56 from the supply spool 114 and through the supply and return floss passageways 52, 54.

With reference next to FIGS. 8B, 13, and 16-19, the stop mechanism 44 is provided to releasably hold the supply floss 56 in place so that when the user actuates the take-up wheel 180, the floss is tensioned along its path between the stop mechanism 44 and the take-up mechanism 50.

Figure 16:
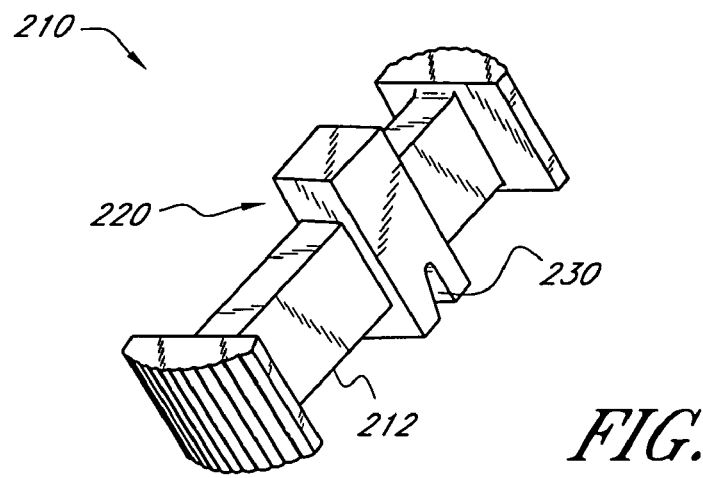
FIG. 16 is a perspective view of a trigger portion.
Figure 17A:
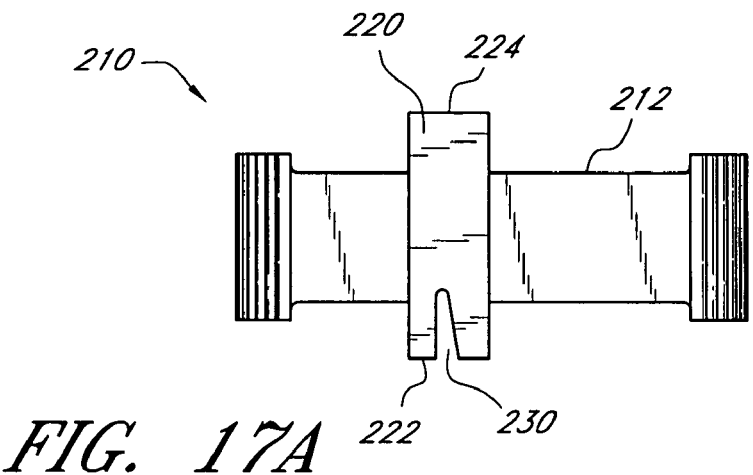
FIG. 17A is an orthographic view of the trigger of FIG. 16.
Figure 17B:
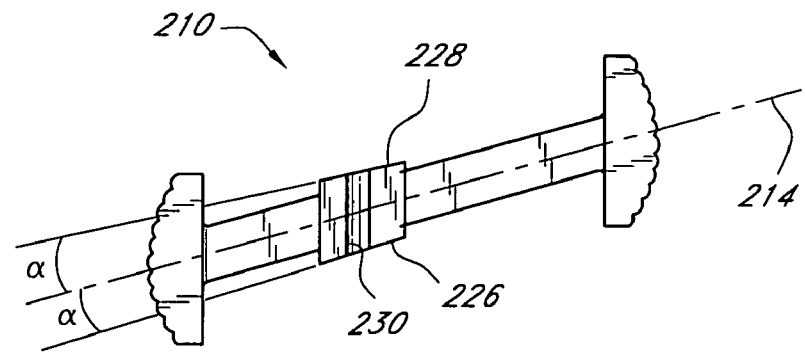
FIG. 17B is a side view of the trigger of FIG. 17A.

With specific reference to FIGS. 16 and 17, the stop mechanism 44 comprises a button or trigger 210. The trigger 210 has an elongate body 212 having a longitudinal axis 214 and a generally transversely extending block 220. The block 220 has first and second side surfaces 222, 224 and front and back surfaces 226, 228. In the illustrated embodiment, the first, second, front and back surfaces are spaced from the body 212 and are generally flat. The second side 224 of the block 220 has a generally "V" shaped slot 230 formed therein.

In the illustrated embodiment, the front and back surfaces 226, 228 are not parallel to the axis 214 of the elongate body 212. Rather, the surfaces 226, 228 are slightly angled toward each other in a "V" fashion. Preferably, the front and back surfaces 226, 228 are disposed at an angle α relative to the axis 214 between about 0 to 10°, more preferably between about 0-5°, and most preferably about 2.5° relative to the body axis.

With specific reference to FIGS. 8A and B, a channel 240 is defined between the front and back stop mechanism walls 150, 146. The channel 240 has a longitudinal axis 242, and is configured so that the block portion 220 of the trigger 210 can slide therein along the longitudinal axis 242. Top and bottom openings 244, 246 are provided through the first and second segments 38, 40. The top and bottom openings 224, 246 are sized to accommodate sliding movement of the elongate trigger body 212, but will not allow the block 220 to slide therethrough.

In the illustrated embodiment, the channel axis 242 is disposed at an angle β relative to a top surface 247 of the housing 32. Similarly, the trigger body 212 is configured to extend and slide at that angle. Preferably the channel axis 242 is disposed at an angle β of between about 60° to 90° relative to the top surface 247 of the housing. More preferably, the angle β is between about 70° to 80°, and most preferably β is about 75°.

In the illustrated embodiment, the front and back stop mechanism walls 150, 146 are not completely parallel to one another. For example, in the illustrated embodiment, each of the walls is generally at an angle γ that differs from the channel axis 242 by about 0-10°. More preferably, the walls are within 0-5° of the channel axis and most preferably angle γ is about 2.5° relative to the channel axis. As such, the walls when considered together are generally "V" shaped.

Figure 18:
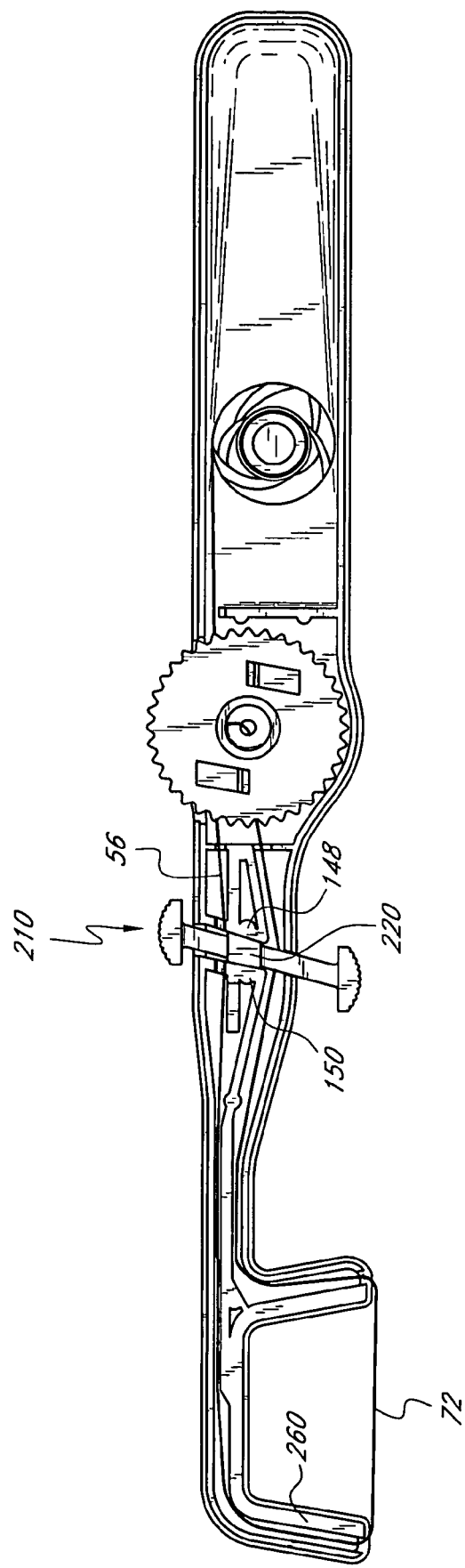
FIG. 18 shows the interior of the device with the trigger in a down position.

In a preferred embodiment the "V" shape of the walls corresponds to the "V" shape of the front and back surfaces 226, 228 of the trigger block 220. Thus, depending on the position of the trigger 210 within the channel 240, the fit and ease of motion of the trigger varies. For example, FIG. 9 shows the trigger 210 in a relatively loose "open" configuration. In this position, the trigger can move relatively freely in relation to the channel walls 150, 146. As the trigger 210 is pushed downwardly, the front and back block surfaces 226, 228 engage the front and back walls 150, 146, thus creating a resistant friction force. As the trigger 210 moves further downwardly, the fit of the block 220 between the front and back walls 150, 146 becomes tighter and the friction force incrementally increases until reaching a maximum friction force when the trigger is in a fully down position as shown in FIG. 18. As shown, the trigger block 220 and the walls 150, 146 preferably are configured so that the block 220 does not extend downwardly below the elongate rib 142. As such, the return floss pathway 54 remains unobstructed by the trigger block.

With reference again to FIGS. 8B, 9 and 18-19, "V" shaped slots 248, 250 are formed in each of the front and back stop mechanism walls 150, 146 to define the supply path 52 therethrough. Preferably a base portion 252 of each "V" slot is spaced from the second segment side wall 75. The "V" notches 248, 250 in the front and back wall 150, 146 cooperate with the "V" notch 230 in the trigger block 220 so as to provide a small opening 256 through the stop mechanism 44. As shown, the wall "V" notches 248, 250 and block "V" notch 230 are disposed in generally opposite directions so that they cooperate to provide the opening 256. Due to this cooperation, the stop mechanism opening 256, through which the supply floss 56 passes, is spaced from the side wall 75, and its position is tightly controlled so that there is relatively little room for the floss to move transversely within the supply path. This becomes helpful in the operation of the stop mechanism, as will be discussed below.

Figure 19:
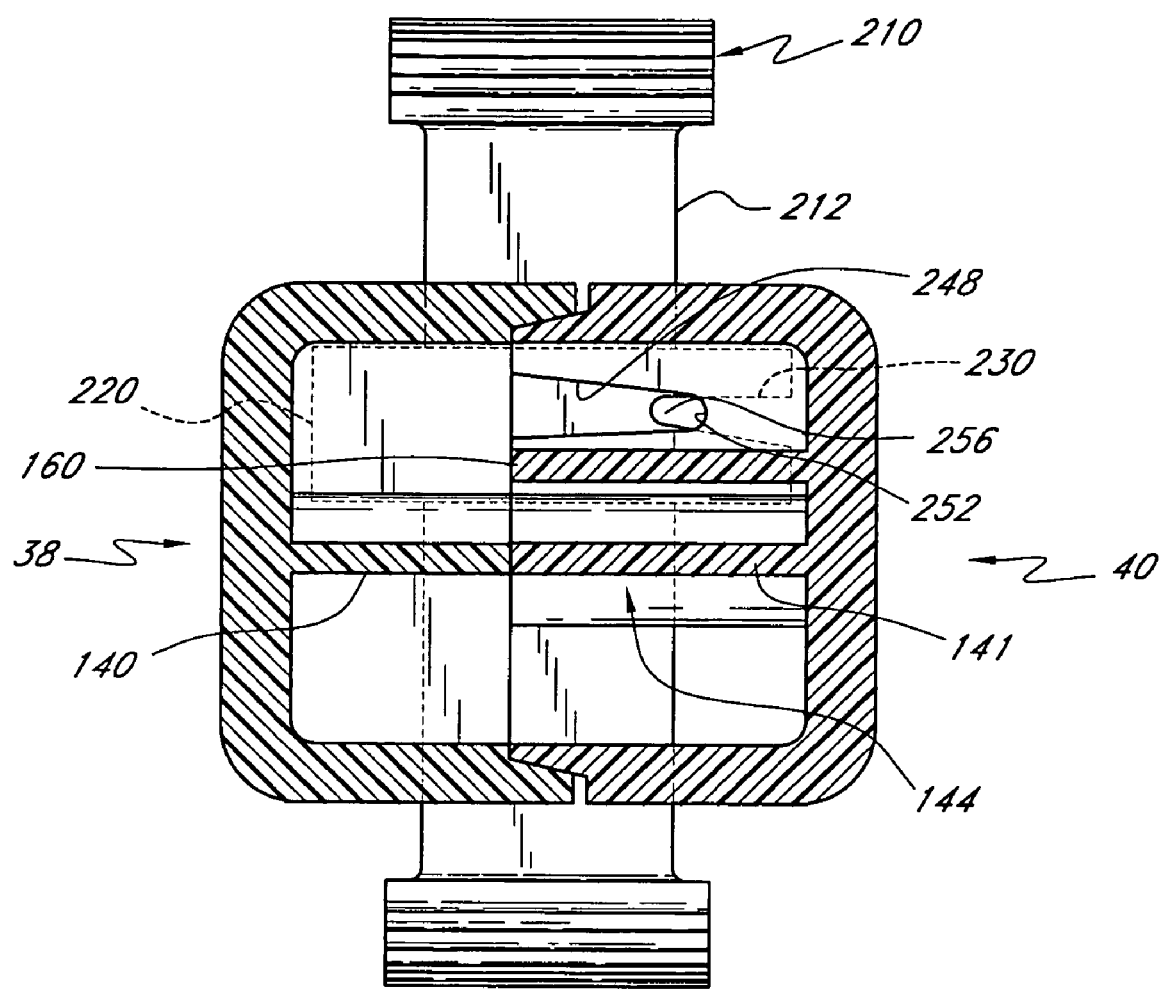
FIG. 19 is a cross-section of the flossing device of FIG. 10 taken along line 19-19.

When the trigger block V-notch 200 is substantially aligned with the stop mechanism wall notches 248, 250 as shown in FIGS. 9 and 19, the floss 56 can be moved along the supply path 52 and through the aligned notches with very little or no resistance. However, as the trigger 210 is actuated by being pressed downwardly, as shown in FIG. 18, the block V-notch 230 is no longer aligned with the wall notches 248, 250, and the path of the floss 56 through the notches becomes tortuous, thus increasing resistance. Additionally, as discussed above, as the trigger 210 is moved downwardly, the front and back surfaces 226, 228 of the block 220 engage the surfaces of the front and back walls 150, 146 in a friction fit. The floss is included in this friction fit, causing further resistance to floss advancement. In the illustrated embodiment, the greatest frictional resistance is achieved as the trigger is pushed to its down-most position as shown in FIG. 18. The frictional resistance is continuously variable between the free flowing position shown in FIG. 9 and the maximum resistance shown in FIG. 18. Such resistance increases in a gradient fashion as the trigger is moved downwardly.

Certain structural characteristics of the illustrated embodiment aid the performance of the stop mechanism. For example, the first, second and third rib portions 144, 160, 162 provide significant reinforcement and support for the front and back walls 150, 146. As such, even though a significant force is exerted on the walls by the trigger block surfaces, the walls will experience very little or no deformation, and any deformation will be consistent and predictable over time. Additionally, the reinforcement ribs help the walls 150, 146 not to degrade in their friction fit response over time. Further, the second and third ribs 160, 162 are arranged adjacent the top "V" notches 248, 250 on the walls. This provides further reinforcement as the floss enters the stop mechanism, and the elongate rib 142 helps ensure that the trigger block does not extend downwardly beyond its desired range in the channel. Still further, the cooperating notches are arranged so that the opening 256 is spaced from the side walls 74, 75 and is relatively small. This minimizes play that may occur in the floss during use, and prevents the side walls from interfering with the floss.

As discussed above, in operation, the stop mechanism 44 selectively immobilizes the supply of floss so that actuation of the take-up mechanism 50 imparts tension upon the floss between the stop mechanism and the take-up mechanism. As such, the floss in the exposed area is under tension, as is appropriate during use, and as is set by the user. In a preferred embodiment, the flossing device has a tension operating range wherein at least three pounds of tension is applied to the floss. More preferably, tension during operation is between about 4-15 lbs., and even more preferably is between about 4-9 lbs. Still more preferably the operating tension is between about 5-8 lbs., and most preferably is between about 7-8 lbs. Such operating tension is set by the user actuating the stop mechanism 44 and then actuating the take-up mechanism 50 to apply the tension.

As the device is being used, it can be expected that the interaction of the user's teeth with the device can cause spikes of high tension for short periods of time. As such, there may be some minor variation in the tension in the floss during operation. In a preferred embodiment, the flosser uses a high strength floss material, having a yield limit of between about 20-50 lbs. of tension. Thus, even when the device is operated at a regulated operating tension of between about 7-10 or 7-8 lbs., variations in that tension can be accommodated without the floss breaking.

As discussed above, when the floss exceeds a tension equal to the resistant force applied by the stop mechanism, the floss will slip relative to the stop mechanism. In a preferred embodiment, the stop mechanism 44 is configured so that when the trigger 210 is fully actuated, the floss will slip when more than about 10 lbs. of tension is applied. In another embodiment, the maximum slip tension limit is about 9 lbs. In a still further embodiment, the stop mechanism 44 and take-up mechanism 50 are configured so that the device can apply up to about 15 lbs. of tension in the floss before the stop mechanism allows slippage of the floss. Of course, the user can adjust the position of the trigger so that slippage begins at any tension between zero and the maximum slip tension. Preferably the trigger does not fully release when the slip tension limit is exceeded. Rather, when tension in the floss exceeds the tension limit, the floss tension overcomes the friction fit of the stop mechanism and slips relative to the stop mechanism. The stop mechanism remains engaged, and holds for applied tensions less than the slip tension limit.

As just discussed, the flossing device described herein is configured to exert relatively high tension upon floss. As such, the device preferably is manufactured to operate at such tensions without failure. Similarly, the device is configured to accommodate floss in a manner so that the floss will not fail when repeatedly subjected to high tensions over the life of the device.

As discussed above and with reference again to FIGS. 1 and 8A and B, the flosser head 36 has a modified "F" type shape. The head 36 comprises the tines 60, 70 and the back portion 166. The outer surface of the head 36 preferably is rounded about its edges so as to avoid causing trauma to the user's mouth. Additionally, the tines 60, 70 and back 166 of the flosser 30 are relatively small in order to fit comfortably in the user's mouth.

With reference to FIGS. 2, 3 and 8A and B, the back 166 of the flosser head 36 preferably extends in a direction generally the same as the direction of the top surface 247 of the housing 32. The distal tine 60 extends downwardly from the back 166, and is inclined downwardly and distally at an angle δ of about 78-81 degrees relative to the back 166. More preferably, the distal tine 60 is angled about 79-80 degrees relative to the back. The proximal tine 70 also extends downwardly from the back 166 and preferably is inclined downwardly and proximally relative to the back at an angle µ between about 78-81 degrees. More preferably, the proximal tine 70 is angled about 79-80 degrees relative to the back. As such, although the proximal and distal tines extend downwardly, they are inclined in generally opposite directions, and the tines 60, 70, back 166 and the floss 72 extending between the tines together make up a trapezoidal truss structure. This truss structure is configured to withstand relatively high floss tensions with controlled flex of the tines and without breakage of the device or the floss.

Excess or uncontrolled flexure in the tines and/or housing while the floss is tensioned can result in inconsistent tensioning during use. In the illustrated embodiment, the tines 60, 70 flex toward each other less than about 5-15% when subjected to tensions within the operating range of the device. This deflection is measured as the difference in the distance between the tines at the floss exit and entrance points. In one embodiment, the maximum operating tension is about 8 pounds, and the tines deflect about 5-15% at maximum tension. More preferably, the tines deflect about 8-12%, and most preferably about 10%.

With specific reference next to FIGS. 8B and 9, a tine reinforcement portion 260 of the second segment 40 peripheral edge 90 is thickened relative to the housing wall 75, 77 in the rest of the tines and back. This thickened portion 260 contributes to the strength and durability of the head 36 when under floss tension. It also supports the high strength floss, which may cut through a thinner material when subjected to stress. As such, the reinforcement portion 260 is configured so that floss at the maximum operating tension of the device will not cut through the portion. In the illustrated embodiment, the thickened portion 260 is at least twice as thick as the top and side walls 77, 75 in the tines and back. Also, the thickened portion 260, preferably is greater than one-half the width of the floss supply path 53 within the flosser head back.

The reinforced portion 260 also extends outwardly from the head side wall 75 so that, when the segments 38, 40 are assembled to form the housing 32, the portion 260 overlaps the opposing segment 38 at least to the extent of the floss path openings 62, 64. In the illustrated embodiment, a pair of energy directors 157 extend from the first segment side wall 74, and are sized and configured to preferentially melt during sonic welding, or other welding manufacturing methods, in order to securely bond the reinforced portion 260 to the side wall 74. As such, the reinforced portion 260 extends substantially all the way across the floss path openings 62, 64, and floss under tension is engaged and supported by the reinforced portion 260.

In the illustrated embodiment, the reinforced portion 260 is thickened relative to the adjacent side and top walls 75, 77. In another embodiment, the reinforced portion comprises a different material than the adjacent side and top walls. For example, the reinforced portion may comprise an insert constructed of a rigid material such as metal, cured epoxy, polycarbonate or the like. Preferably the insert comprises a material more rigid than the adjacent side and top walls.

As discussed above, the illustrated flossing device 30 embodiment employs a relatively high-strength floss. In a preferred embodiment, the relatively high strength floss comprises a high molecular weight polyethylene fiber marketed by Honeywell under the trademark "Spectra." Preferably, the floss contains a multi-filament combination of such fibers, and the combination is treated in order to obtain desirable surface characteristics. Floss treatment can be achieved through various methods and apparatus. In a preferred embodiment, the floss is covered with at least one coat of wax in order to obtain desirable surface characteristics. Such application of wax can be by any of a variety of methods, and multiple coats of wax can also be applied.

In a preferred embodiment, the floss is covered with two coats of multi-wax. These layers of multi-wax may have different characteristics or may be relatively similar to one another. A coat of beeswax, or a wax combination comprising beeswax, preferably is applied over the multi-wax so as to encapsulate the multi-wax within the layer of beeswax.

The multi-wax can include various additives to enhance the floss's capabilities. For example, one or more of the multi-wax layers can include a flavoring additive. Another additive that can be added to one or more layers of the multi-wax is an anti-bacterial agent, such as sodium benzoate, xylitol or thymol. Multi-wax is generally water soluble. As such, in the presence of water, the wax generally dissolves and/or degrades. Accordingly, when the wax is used, additives within the wax are released in the user's mouth. However, if multi-wax is exposed to water prior to use, it may dissolve and/or degrade prematurely. If the multi-wax were to degrade prematurely in a device having aspects of the flossing device embodiments discussed herein, water damage to the floss could occur, for example, in cases of high humidity and/or leakage through the device if a user submerges all or part of the device. In such a device, the degrading wax could clog up the pathways, gum up the device, and decrease the efficiency and consistency of stop mechanism operation. By covering the multi-wax with a non-water soluble layer of beeswax, the water soluble multi-wax is protected from water and the associated flossing device is protected from problems that could result from such high humidity and/or water leakage.

Beeswax also lends other advantages to embodiments of the flossing device. For example, beeswax tends to allow the floss to slip more easily through the user's teeth and is thus more comfortable. Further, although other types of floss may remove plaque and dental caries from teeth, the dislodged plaque may remain in the user's mouth. Conversely, beeswax has a tendency to adhere to particulates such as plaque. Thus, plaque removed from a user's teeth by the floss has a tendency to bind to the beeswax and be removed with the floss from the user's mouth.

By encapsulating the multi-wax in non-water soluble beeswax, flavors and other additives in the multi-wax are preserved because the beeswax does not deteriorate over time or if exposed to humidity. Of course, use of the floss in the user's mouth will disrupt the beeswax's encapsulation, enabling the water soluble multi-wax to contact water within the user's mouth and deliver additives, medicaments and the like.

The embodiment discussed above employs a multi-filament floss that is covered with one or two coats of water soluble multi-wax which are then encapsulated by a coat of beeswax. It is to be understood that, in other embodiments, more or less layers of wax can be employed, and other types of water-soluble or non-water-soluble wax can also be used. Furthermore, although beeswax has been disclosed as a preferred wax for encapsulation, other known generally non-water soluble waxes, such as carnuba wax and candle wax, can be used in order to help preserve inner layers of wax and preserve the integrity of the pathways and stop mechanism of the flossing device. Additionally, beeswax can be combined with multi-wax to create a wax layer with improved water resistance and preservative properties.

With reference again to FIG. 9, and as discussed above, the floss supply spool 114 has supply floss 56 wound about it. As the take-up wheel 170 is actuated, and floss is advanced through the supply and return paths 52, 54, floss 56 unwinds from the spool 114. As also discussed above, in the illustrated embodiment, the stop mechanism 44 and take-up wheel 170 are arranged so that when high tension is applied to the floss, the portion of the floss subjected to the high tension is that portion between the stop mechanism 44 and take-up wheel 170. The floss supply spool 114 remains generally loose. The coating of beeswax in the floss of the above-discussed embodiment generally is relatively sticky so that floss that is wound over itself on the supply spool 114 is mildly bonded to itself. This mild bond between windings prevents spontaneous unwinding of the generally loose supply bobbin. As such, knotting and clogging of the supply floss 56 is minimized or eliminated.

Although beeswax is used for an outer wax coating in the above-described embodiment, it is to be understood that other types of coatings, whether wax or non-wax, can also be used for similar purposes. Preferably, such a coating has properties such that when the floss is wound upon itself, adjacent windings are mildly bonded together, thus resisting spontaneous unwinding or loosening of the floss upon the spool; however, the bond between floss windings preferably is sufficiently mild that it does not appreciably resist unwinding when the take-up wheel is actuated to advance floss to the device.

As discussed above, additives such as flavoring and anti-bacterial medicaments can be added to the wax coatings that are disposed on the floss. Generally, these additives are delivered to the user's mouth during flossing in order to create advantageous effects in the user's mouth.

During use, bacteria and other matter from the user's mouth are transferred to the floss, which is wound upon the take-up wheel after use. This is especially true when floss is coated with beeswax, which has a tendency to bind to particulate matter. In the illustrated embodiment, used floss 58 is wound upon the take-up wheel 170 and is repeatedly subjected to relatively high tensions over the life of the flossing device 30. Over time, bacteria may degrade the floss, and the floss may become prone to failure during the repeated tensions. Thus, in accordance with still another embodiment, an anti-bacterial additive preferably is added to the floss in order to preserve the floss. In a preferred embodiment, sodium benzoate is added to at least one of the wax coatings on the floss. Sodium benzoate is particularly effective in fighting bacterial growth in a generally acidic environment. Research has indicated that plaque is generally acidic. As discussed above, it is anticipated that plaque will bind with the floss during use. Thus, plaque on the floss on the take-up wheel 170 creates a generally acidic environment on the floss upon the take-up wheel 170. Sodium benzoate is particularly effective for preserving used floss in such an acidic environment. Although sodium benzoate is disclosed in a preferred embodiment, it is to be understood that other additives that have beneficial or advantageous anti-microbial performance in a generally acidic environment can appropriately be used.

Figure 20:
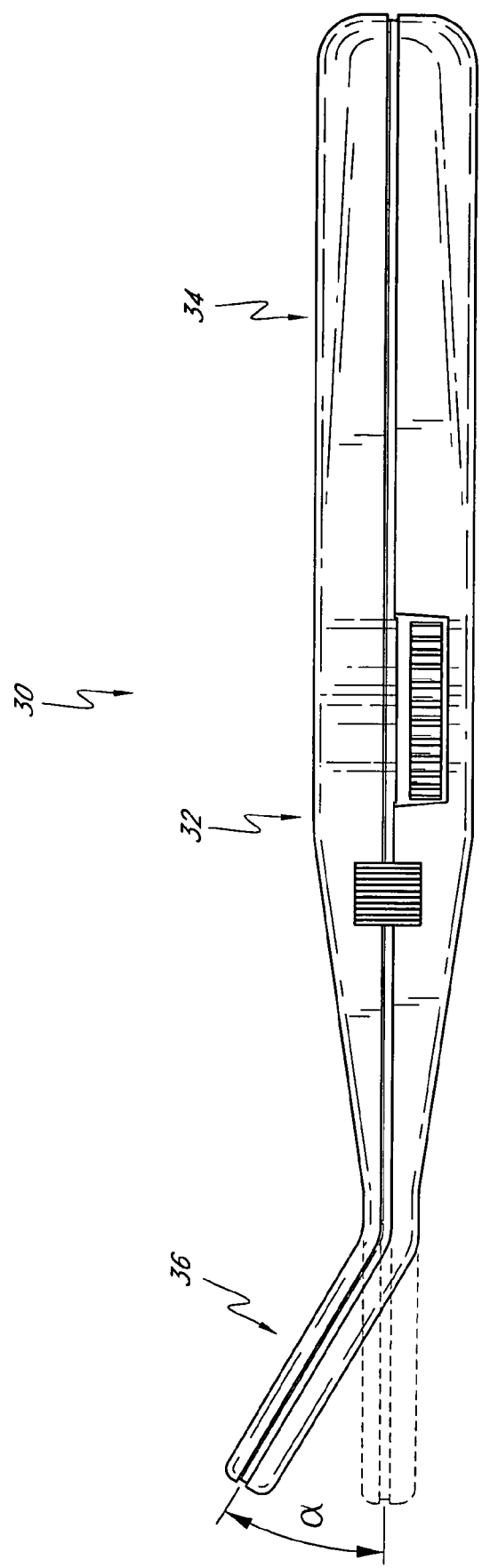
FIG. 20 is a top view of the flossing device of FIG. 1, with the head bent transversely during use.

In a preferred embodiment 30, the housing preferably is formed of a durable plastic such as high impact polystyrene. This material, though sturdy, allows for some bending of the material without failure of the device. Other materials, including polymers such as nylon and noryl, can also be used. The configuration of the ribs 140, 141, 142 within the housing 32 combined with the material allows some lateral deformation of the head 36 without catastrophic failure of the device. For example, with reference to FIG. 20, it is anticipated that some users may wish to bend the head 36 of the device transversely in order to improve access to certain teeth. Preferably, the material used to construct the device when combined with the arrangement of ribs, slots and trusses in the housing is configured so that the device can be deformed up to about 45° without breaking. More preferably, the device can be deformed up to about 30° and even more preferably can be deformed between about 15° to 20° before the head breaks.

In some embodiments, a more rigid material, such as polycarbonate, may be desired. Additionally, further materials may provide additional benefits. For example, some polycarbonates are generally transparent or translucent, enabling a user to visualize the inner workings of the flossing device.

Patients having diseases such as gum diseases can benefit from medications designed to combat these diseases. Such medications include, for example, antibiotics. Such medications can be very powerful, and must be used properly. Typically, the medications are applied by applying a carefully measured dose under the patient's gum line. If the dose varies excessively, the patient could be harmed. As such, it is important that an applicator for such medications be able to strictly control the amount of medication delivered. Traditionally, application of these types of medications has been performed by a clinician. More specifically, patients typically must visit a periodontist in order to have such medications applied. This can be time consuming and expensive.

Figure 21:
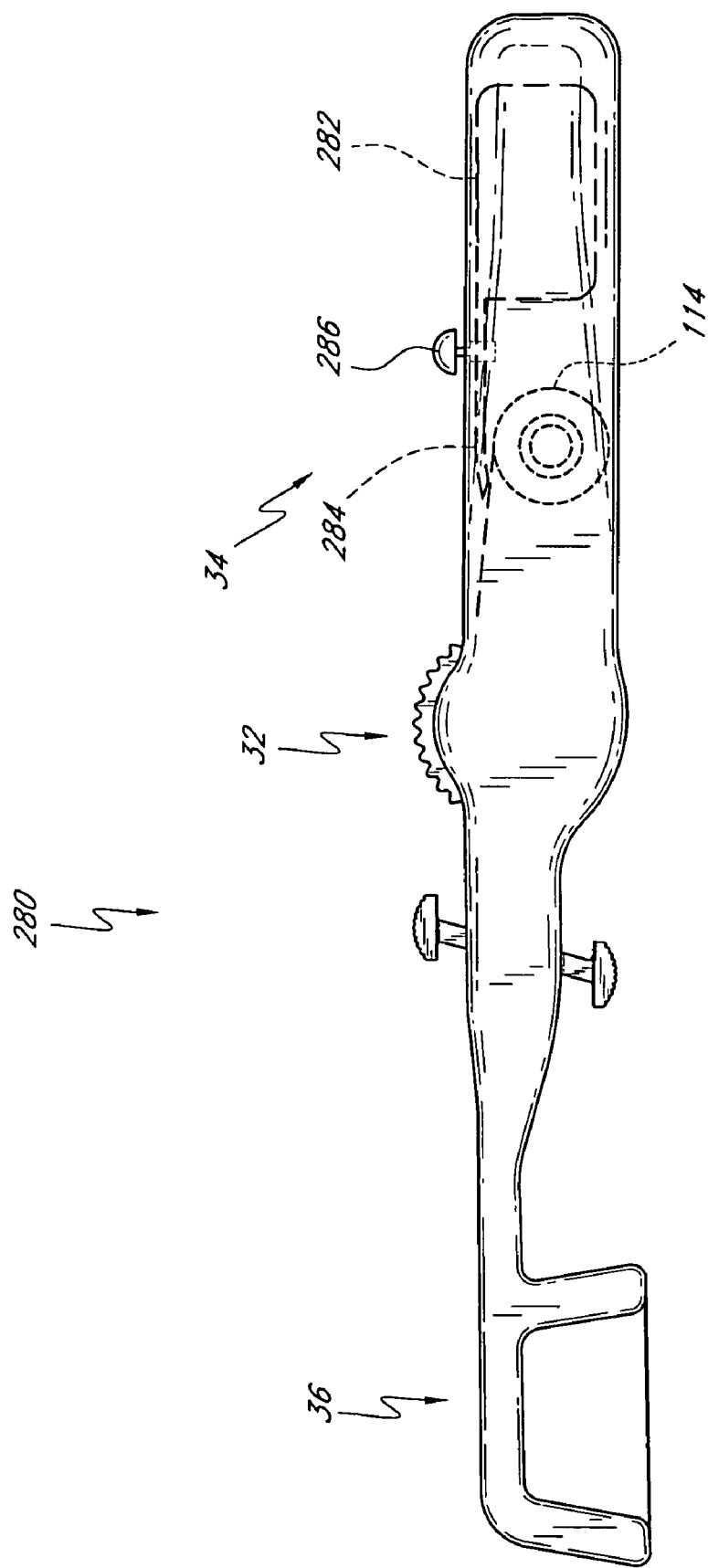
FIG. 21 is a side view showing the inner workings of another embodiment of a flossing device having features of the present invention.

With reference next to FIG. 21, an embodiment of a flossing device 280 is illustrated. The device includes a medicament supply 282 disposed within the handle of the device. A delivery channel 284 directs medication from the medication supply 282 to the supply floss 56. Application of the medicament is controlled by a button 286 that is selectively actuable by the user. As such, a precise amount of medicament can be delivered to the floss so that a closely regulated volume of medication is delivered. For example, the device can be configured so that only a specific volume of medication is delivered per inch of the floss. In use, the patient will be directed to use only that portion of the floss between the tines when flossing the teeth. Thus, the device strictly controls the amount of medicine that is available to be delivered to the patient.

In accordance with another embodiment, floss can be pre-treated to contain the desired volume of medicament per inch of floss. For example, a proper dose of medication can be correlated in terms of volume per unit length, such as mL/in, so that the amount of medication delivered can be closely regulated, yet a user can apply the medication himself rather than go to the added time and expense of a trip to a periodontist.

In yet another embodiment, the patient may add one or more drops of medication directly to the exposed floss 72 between the tines of a flossing device 30. Again, a specific volume of medication is tightly controlled while being delivered to the patient.

Figure 22:
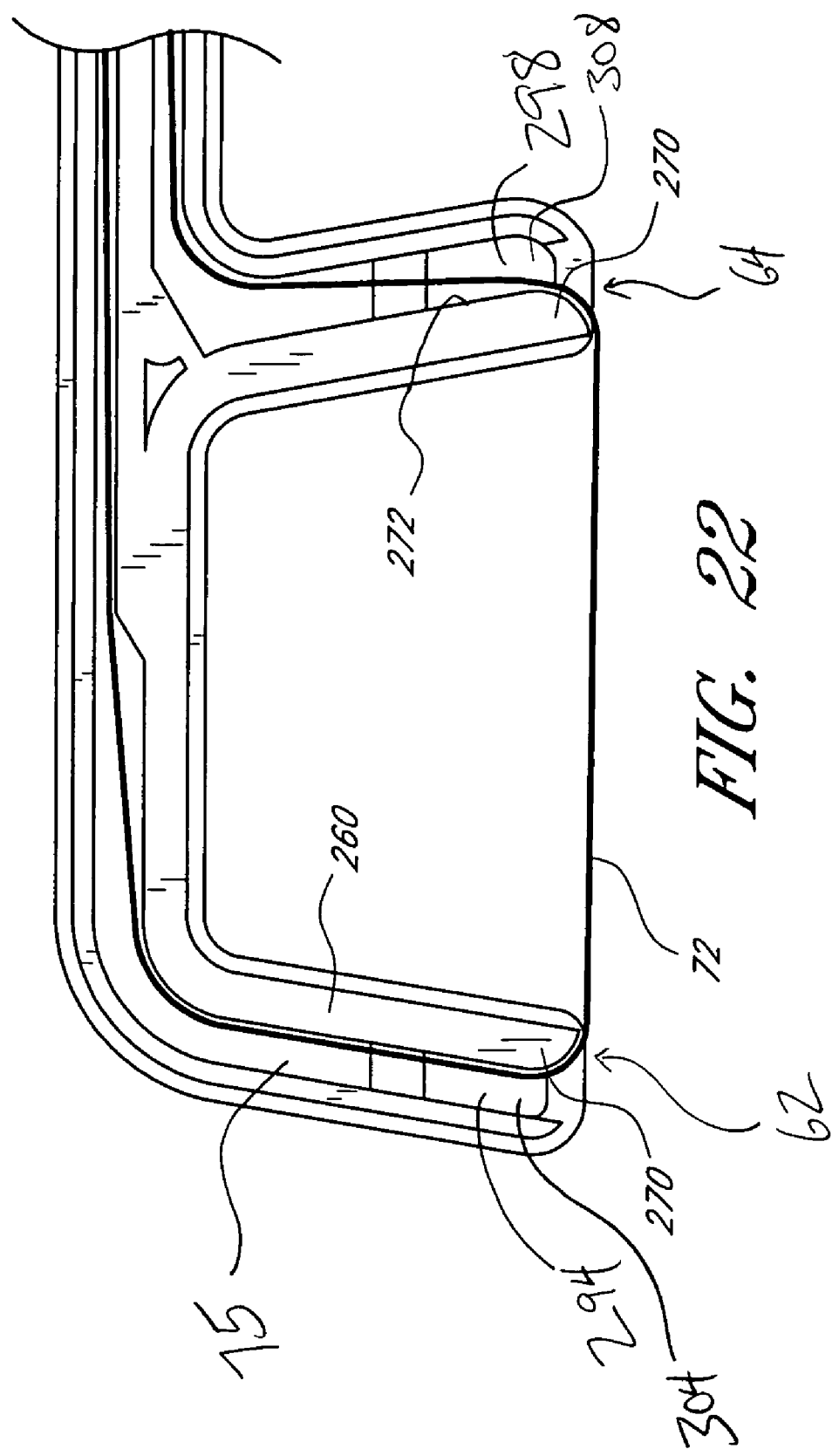
FIG. 22 is a close up view of the inside of the head of another embodiment of a flossing device.

With next reference to FIG. 22, another embodiment of the head portion 36 of the flossing device 30 is disclosed. In the illustrated head portion, the reinforced portion 260 comprises arcuate portions 270 disposed in the inner peripheral surface 272 at the supply floss path exit 62 and the return floss path entrance 64. As discussed above, relatively high tension is often imparted to the floss. In the illustrated embodiment, the arcuate portions 270 are placed at the floss path openings 62, 64, where the path of the floss significantly changes direction. The arcuate portion 270 distribute stresses exerted by the floss on the device material in order to reduce stress concentrations that may be exerted upon the flossing device, thus lessening the tendency to cut or otherwise damage the material.

Figure 23:
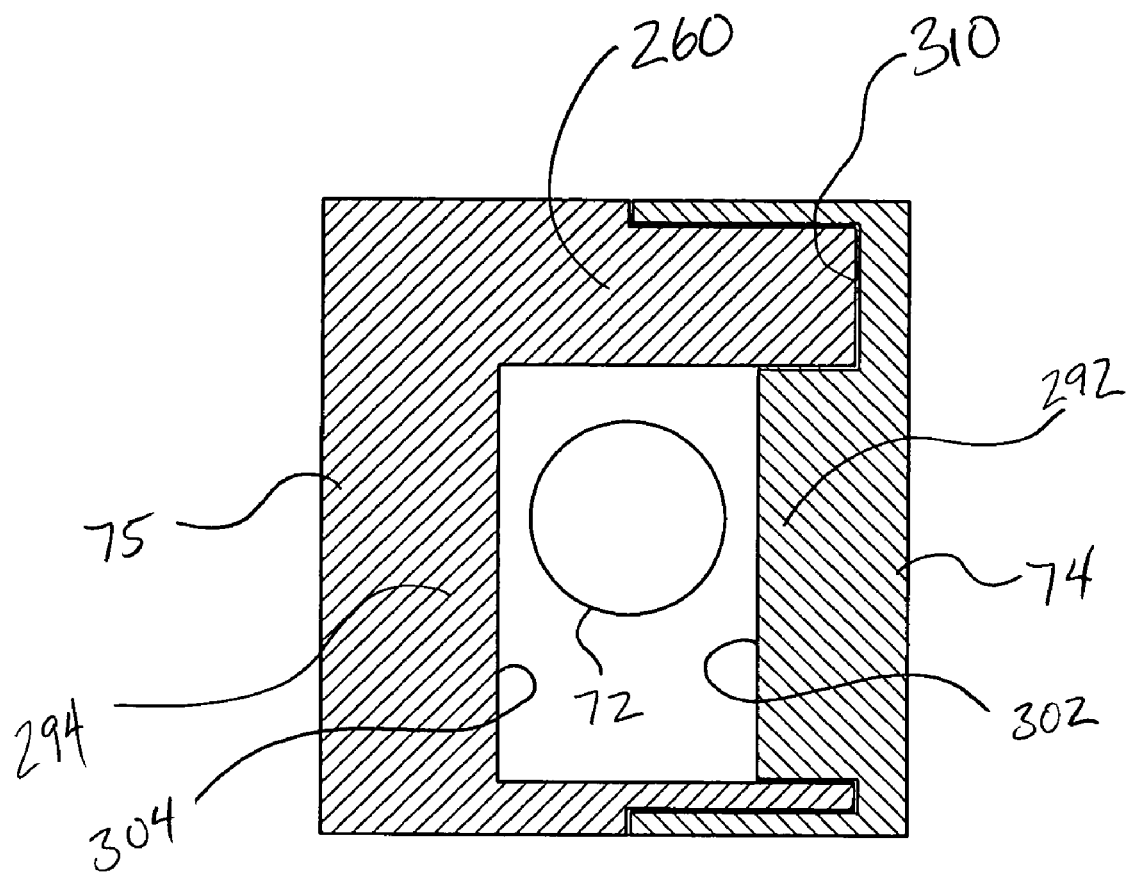
FIG. 23 is a cross-sectional view taken along line 23-23 of FIG. 22.

With reference also to FIGS. 23 and 24A-B, an exit guide portion 292, 294 is arranged on the side wall 74, 75 adjacent the floss exit 62 of each of the first and second segments 38, 40. Similarly, an entrance guide portion 296, 298 is arranged on the side wall 74, 75 adjacent the floss entrance 64 of each of the first and second segments 38, 40. Preferably, the guide portions 292, 294, 296, 298 extend inwardly from the side walls 74, 75 and comprise guide surfaces 302, 304, 306, 308, respectively.

In the embodiment illustrated in FIGS. 23 and 24A-B, the reinforced portion 260 of the head is configured to extend substantially all the way across the floss path openings 62, 64. As best shown in FIG. 23, the reinforced portion 260 engages the side wall 74 at a mating seam 310. the guide portion 292 extends inwardly from the side wall 74 so that there is a space between the guide surface 302 and the mating seam 310. As such, floss 72 is prevented from engaging, and potentially penetrating and compromising, the mating seam 310.

With specific reference to FIGS. 24A and B, in another embodiment, energy directors 312, 314, 316 are arranged along mating edges of the front wall 150, back wall 146, and first portion 144 of the elongate rib 142, respectively. The energy directors 312, 314, 316 preferably comprise relatively thin portions of material that are configured to melt more readily than the adjacent front wall 150, back wall 146, and first portion 144. Thus, the energy directors 312, 314, 316 help to weld the portions thoroughly together during sonic welding of the first and second segments 38, 40. Such strengthening of the flossing device assists in consistent operation of the stop mechanism, as will be discussed in more detail below.

Figure 25:
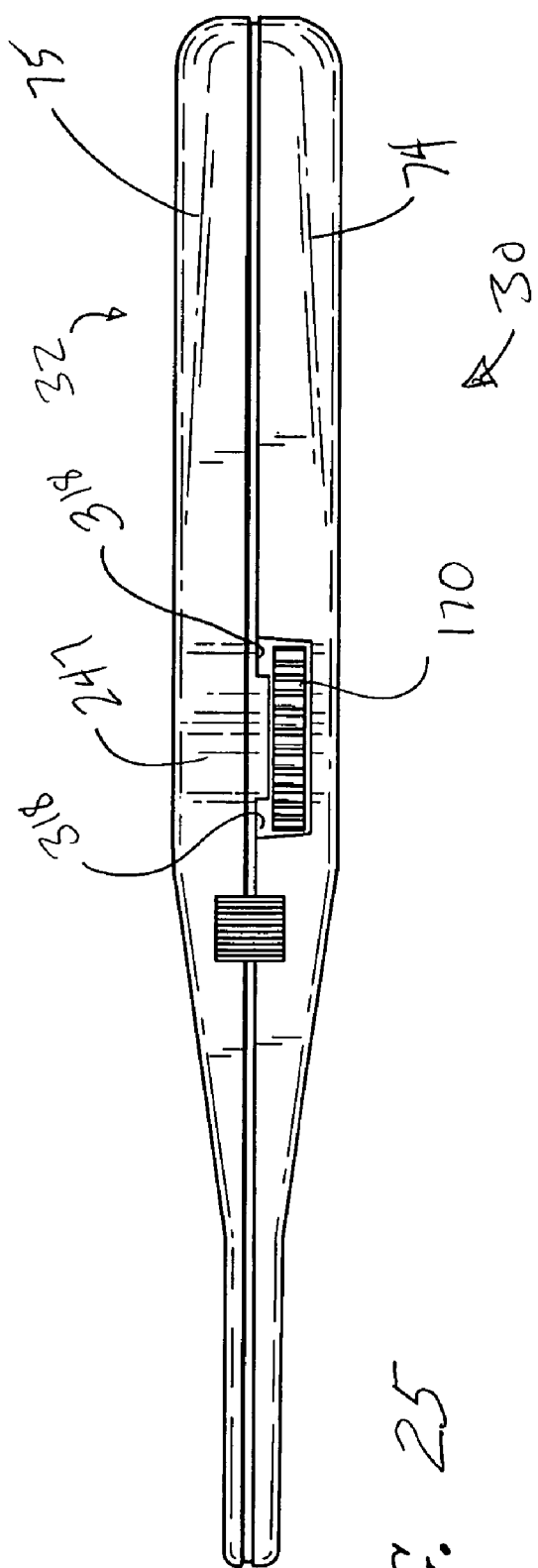
FIG. 25 is a top view of another embodiment of a flossing device.

With reference next to FIG. 25, another embodiment of a flossing device comprises an elongate housing 32 having first and second segments 74, 75 and a top surface 247. A pair of cutouts 318 are formed into the peripheral edge of the top surface 247 of a the second segment 75 so as to generally correspond to the peripheral circumference of the take-up wheel 170. With reference also back to FIG. 15D, the peripheral circumference of the take-up wheel 170 comprises a flanged edge 320. The cutouts 318 generally align with the flanged edge 320, and help prevent or minimize interference between the take-up wheel 170 and the peripheral edge of the second segment 75.

In the illustrated embodiment, the housing is constructed by fitting the two segments together generally in a clam shell manner. It is to be understood that several different methods and apparatus can be used to form the housing, and different shapes of segments and tines can also be used in accordance with aspects of the present invention. For example, in another embodiment, one segment of the housing can incorporate nearly all of the features of the housing and can take up the majority of the housing width. A second segment comprises a cap portion which is relatively thin and fits with the first segment in order to form the enclosed housing.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A hand-held flossing device, comprising:
   a housing having a handle portion and a head portion, the housing supporting a floss supply comprising a floss, a floss path, a floss advancement mechanism configured to selectively advance floss from the floss supply and through the path, and a stop mechanism configured to selectively engage at least a portion of the floss to resist advancement of the floss upon actuation of the advancement mechanism so that a tension is imparted to the floss between the stop mechanism and the advancement mechanism;
   the floss comprising a first surface coating comprising a water soluble material and a second surface coating comprising a generally non-water soluble material, the second coating substantially encapsulating the first coating.

2. The hand-held flossing device of claim 1, wherein the first coating comprises a multi-wax, and the second coating comprises beeswax.

3. The hand-held flossing device of claim 2, wherein the first coating is deposited directly on the floss.

4. A hand-held flossing device, comprising:
   a housing having a handle portion and a head portion;
   a series of ratchet receiver members integrally formed with a wall of the housing;
   a floss supply comprising a floss; and
   a floss supply path defined within the housing between the floss supply and a floss exit formed in the head portion, a floss return path defined within the housing between a floss entrance and an advancement mechanism, a wall disposed between the floss supply path and the floss return path in the housing head portion, floss being directed through the floss supply and return paths, the floss exiting through the exit and reentering through the entrance, an exposed floss portion extending between the exit and entrance;
   wherein the advancement mechanism is configured to selectively advance floss from the supply and through the supply and return paths, and the advancement mechanism comprises a ratcheting member adapted to engage the series of ratcheting receiver members that are integrally formed with the wall of the housing, the ratcheting member being biased outwardly and hinged so that the ratcheting member is moveable over the receiver members only in a first direction and not in a second, generally opposite direction.

5. The flossing device of claim 4, wherein the advancement mechanism comprises a rotatable member having an axle about which floss from the return path is wound, a wheel that rotates with the axle, a portion of the wheel accessible from outside of the housing, and wherein the ratcheting member is disposed on the wheel and is biased outwardly from the wheel.

6. The flossing device of claim 5, wherein the rotatable member comprises a guard that extends radially outward from the axle and rotates with the axle, the guard being spaced from the wheel, and wherein the floss from the return path is wound about the axle between the wheel and the guard.

7. The flossing device of claim 5, wherein the rotatable member is disposed in the handle forwardly of the floss supply, and the floss supply path extends past the rotatable member on a side of the guard opposite the wheel so that the guard is interposed between the floss supply path and the return path floss that is wound about the axle.

8. The flossing device of claim 5, wherein a return path minimum width is the least distance between opposing walls defining the return path along the length of the return path, a supply path minimum width is the least distance between opposing walls defining the supply path along the length of the supply path, and the return path has a minimum width is greater than the supply path minimum width.

9. The flossing device of claim 5, additionally comprising a stop mechanism disposed in the supply path between the floss supply and the advancement mechanism, the stop mechanism configured to selectively prevent advancement of the floss.

10. The flossing device of claim 9, wherein the stop mechanism comprises a friction lock, and the friction lock and advancement member are configured so that a user can selectively apply between about 0-15 pounds of tension to floss between the stop mechanism and the advancement mechanism.

11. The flossing device of claim 10, wherein the user can selectively apply between about 0-10 pounds of tension to the floss, and the stop mechanism and advancement mechanism are actuable by one of the user's hands holding the device.

12. The flossing device of claim 10, wherein the friction lock comprises a movable member and a stationary member, wherein the floss is selectively pinched between the movable and stationary members, and the stationary member comprises a truss configured to prevent substantial deflection when the movable member engages the stationary member.

13. The flossing device of claim 5, wherein the ratchet receiver members are integrally formed on a wall of the housing that is generally transverse to a longitudinal axis of the rotatable member axle and are arranged in a generally circular array, and the ratcheting member on the wheel engages the ratchet receiver members 14. The flossing device of claim 13, wherein the ratcheting member comprises a pawl extending from a side surface of the wheel.

15. The flossing device of claim 14, wherein the floss supply path is arranged so as to pass between the guard and a first side wall of the housing.

16. The flossing device of claim 15, wherein the advancement mechanism comprises a ratcheting member configured to allow rotation of the axle in only a first rotational direction.

17. The flossing device of claim 16, wherein a plurality of ratchet receiver members are integrally formed with a second side wall of the housing and are arranged in a generally circular array, the second side wall being generally opposite the first side wall, and the wheel comprises a ratcheting member that is biased outwardly from the wheel and hinged relative to the wheel so that the ratcheting member is moveable over the receiver members when the wheel is rotated in the first rotational direction.

18. The flossing device of claim 16, wherein the floss supply path is defined between the divider wall and a first wall opposite the divider wall, and the floss return path is defined between the divider wall and a second wall opposite the divider wall, a minimum supply path width is defined as the minimum distance between the divider wall and the first wall along the length of the floss supply path, and a minimum return path width is defined as the minimum distance between the divider wall and the second wall along the length of the floss return path, wherein the minimum return path width is greater than the minimum supply path width.

19. A hand-held flossing device, comprising:
a housing having a handle portion a head portion, and a longitudinal axis, the housing having an outer wall extending circumferentially about the longitudinal axis;
a floss supply comprising a floss;
a floss supply path defined within the housing between the floss supply and a floss exit formed in the head portion; and
a floss return path defined within the housing between a floss entrance and an advancement mechanism, the advancement mechanism configured to selectively advance floss from the floss supply and through the supply and return paths; and
a stop mechanism interposed between the floss supply and floss exist, the stop mechanism comprising a front stop wall, a rear stop wall, and a stop member, the stop member selectively movable between a first position and a second position, wherein in 20. The flossing device of claim 19, wherein the device is made of a polymer, and the truss structure and polymer are configured so that if the head of the flossing device is bent up to about 45°, the structural integrity of the floss supply and return paths is preserved.

21. The hand-held flossing device of claim 19, wherein each of the front and rear stop walls is part of an enclosed a-truss structure, a front stop truss structure comprising the front stop wall and at least two ribs that extend generally forwardly from the front stop wall, a rear stop struss structure comprising the rear stop wall and at least two ribs that extend generally rearwardly from the rear stop wall.

22. The flossing device of claim 21, wherein the stop mechanism has a maximum tension limit, and the stop mechanism is configured so that if tension in the floss exceeds the maximum tension limit, the floss will slip relative to the stop mechanism.

23. The flossing device of claim 22, wherein the floss has a yield strength greater than the maximum tension limit.

24. The flossing device of claim 23, wherein the floss has a yield strength greater than about 20 pounds.

25. The flossing device of claim 24, wherein the maximum tension limit is less than about 15 pounds.

26. A hand-held flossing device, comprising:
a housing having a handle portion and a head portion;
a floss supply comprising a floss, the floss supply disposed in the handle portion;
an advancement mechanism supported by the housing and interposed between the floss supply and the head portion;
a floss supply path defined within the housing between the floss supply and a floss exit formed in the head portion, a floss return path defined within the housing between a floss entrance and the advancement mechanism, a divider wall disposed between the floss supply path and the floss return path in the housing head portion;
wherein the device is configured so that floss is directed from the floss supply through the floss supply path to the exit and reenters through the entrance so that an exposed floss portion extends between the exit and entrance, and wherein floss is further directed along the return path from the entrance to the advancement mechanism;
wherein the advancement mechanism comprises an axle rotatably supported by the housing, a wheel that extends radially from the axle and rotates with the axle, and a guard that extends radially from the axle and rotates with the axle, a space being disposed between the wheel and the guard, floss from the return path being wound about the axle in the space between the wheel and the guard so that selective rotation of the wheel selectively advances floss from the floss supply through the supply and return paths and to the advancement mechanism; and
wherein the floss supply path is arranged in the housing so as to pass by the advancement mechanism on a side of the guard opposite the wheel so that the guard is interposed between the floss supply path and the return path floss that is wound about the axle.

* * * * *